US010485850B2

(12) United States Patent
Prestrelski et al.

(10) Patent No.: US 10,485,850 B2
(45) Date of Patent: Nov. 26, 2019

(54) METHODS FOR PRODUCING STABLE THERAPEUTIC FORMULATIONS IN APROTIC POLAR SOLVENTS

(71) Applicant: Xeris Pharmaceuticals, Inc., Chicago, IL (US)

(72) Inventors: Steven Prestrelski, Chicago, IL (US); Michael Sandoval, Chicago, IL (US); Martin Donovan, Chicago, IL (US)

(73) Assignee: XERIS PHARMACEUTICALS, INC., Chicago, IL (US)

( * ) Notice: Subject to any disclaimer, the term of this patent is extended or adjusted under 35 U.S.C. 154(b) by 0 days.

(21) Appl. No.: 15/594,998

(22) Filed: May 15, 2017

(65) Prior Publication Data

US 2017/0312341 A1    Nov. 2, 2017

Related U.S. Application Data

(63) Continuation of application No. 15/136,650, filed on Apr. 22, 2016, now Pat. No. 9,649,364.

(60) Provisional application No. 62/233,032, filed on Sep. 25, 2015.

(51) Int. Cl.
| | | |
|---|---|---|
| *A61K 38/26* | (2006.01) | |
| *A61K 9/00* | (2006.01) | |
| *A61K 47/02* | (2006.01) | |
| *A61K 47/10* | (2017.01) | |
| *A61K 47/20* | (2006.01) | |
| *A61K 47/26* | (2006.01) | |
| *A61K 38/00* | (2006.01) | |
| *A61K 47/00* | (2006.01) | |
| *A61K 47/12* | (2006.01) | |
| *A61K 9/08* | (2006.01) | |
| *A61M 5/142* | (2006.01) | |
| *A61K 47/18* | (2017.01) | |
| *A61M 5/32* | (2006.01) | |

(52) U.S. Cl.
CPC .......... *A61K 38/26* (2013.01); *A61K 9/0019* (2013.01); *A61K 9/08* (2013.01); *A61K 38/00* (2013.01); *A61K 47/00* (2013.01); *A61K 47/02* (2013.01); *A61K 47/10* (2013.01); *A61K 47/12* (2013.01); *A61K 47/183* (2013.01); *A61K 47/186* (2013.01); *A61K 47/20* (2013.01); *A61K 47/26* (2013.01); *A61M 5/142* (2013.01); *A61M 5/32* (2013.01)

(58) Field of Classification Search
CPC ...... A61K 38/26; A61K 9/0019; A61K 47/02; A61K 47/10; A61K 47/20; A61K 47/26; A61K 38/00; A61K 47/00; A61K 47/12; A61K 9/08; A61K 47/183; A61K 47/186; A61M 5/142; A61M 5/32
See application file for complete search history.

(56) References Cited

U.S. PATENT DOCUMENTS

| | | | |
|---|---|---|---|
| 3,016,895 A | 1/1962 | Sein | 604/60 |
| 4,608,764 A | 9/1986 | Leuenberger | 34/295 |
| 4,848,094 A | 7/1989 | Davis et al. | 62/64 |
| 4,927,571 A | 5/1990 | Huang et al. | 264/4.3 |
| 5,031,336 A | 7/1991 | Diesner et al. | 34/287 |
| 5,092,843 A | 3/1992 | Monroe et al. | 604/138 |
| 5,208,998 A | 5/1993 | Oyler | 34/288 |
| 5,260,306 A | 11/1993 | Boardman et al. | 514/291 |
| 5,716,640 A | 2/1998 | Kamei et al. | 524/451 |
| 5,932,547 A | 8/1999 | Stevenson et al. | 514/10.3 |
| 5,977,082 A | 11/1999 | Gatti et al. | 514/34 |
| 6,001,336 A | 12/1999 | Gordon | 424/46 |
| 6,051,256 A | 4/2000 | Platz et al. | 424/489 |
| 6,124,261 A | 9/2000 | Stevenson et al. | 514/2.4 |
| 6,199,297 B1 | 3/2001 | Wisniewski | 34/284 |
| 6,253,463 B1 | 7/2001 | Hansen | 34/362 |
| 6,264,990 B1 | 7/2001 | Knepp et al. | 424/499 |
| 6,290,991 B1 | 9/2001 | Roser et al. | 424/502 |
| 6,309,663 B1 | 10/2001 | Patel et al. | 424/450 |
| 6,331,310 B1 | 12/2001 | Roser et al. | 424/423 |
| 6,371,939 B2 | 4/2002 | Bergens et al. | 604/156 |
| 6,495,164 B1 | 12/2002 | Ramstack et al. | 424/489 |
| 6,667,061 B2 | 12/2003 | Ramstack et al. | 424/489 |
| 6,676,958 B2 | 1/2004 | Gerber | 424/434 |
| 6,730,328 B2 | 5/2004 | Maskiewicz et al. | 424/499 |
| 7,005,421 B2 | 2/2006 | Gatti et al. | 514/34 |
| 7,163,704 B2 | 1/2007 | Zhang | 424/725 |
| 7,259,225 B2 | 8/2007 | Song et al. | 528/272 |

(Continued)

FOREIGN PATENT DOCUMENTS

| | | |
|---|---|---|
| CN | 1507858 | 6/2004 |
| CN | 101842079 | 9/2010 |

(Continued)

OTHER PUBLICATIONS

Zhang et al, Antimicrobial peptides, Current Biology, 2016, 26, pp. R14-R19.*

(Continued)

*Primary Examiner* — Karlheinz R. Skowronek
*Assistant Examiner* — Li N Komatsu
(74) *Attorney, Agent, or Firm* — Norton Rose Fulbright US LLP

(57) ABSTRACT

Certain embodiments are directed to a formulation of a therapeutic agent, as well as a method of making such a formulation, comprising at least one therapeutic agent dissolved in an aprotic polar solvent system comprising at least one ionization stabilizing excipient in a concentration sufficient to impart physical and chemical stability to the therapeutic agent.

12 Claims, 2 Drawing Sheets

(56) References Cited

U.S. PATENT DOCUMENTS

| | | | |
|---|---|---|---|
| 7,314,636 B2 | 1/2008 | Caseres et al. | 424/426 |
| 7,371,406 B2 | 5/2008 | Rasstack et al. | 424/489 |
| 7,396,841 B2 | 7/2008 | Doen et al. | 514/338 |
| 7,442,832 B2 | 10/2008 | Gentile et al. | 562/460 |
| 7,498,312 B2 | 3/2009 | Cohen et al. | 514/36 |
| 7,582,311 B1 | 9/2009 | Cleland et al. | 424/489 |
| 7,604,822 B2 | 10/2009 | Ionascu | 424/725.1 |
| 7,651,703 B2 | 1/2010 | Cleland et al. | 424/489 |
| 7,915,229 B2 | 3/2011 | Cohen et al. | 514/36 |
| 8,110,209 B2 | 2/2012 | Prestrelski et al. | 424/423 |
| 2002/0179647 A1 | 12/2002 | Hall et al. | 222/175 |
| 2003/0026884 A1 | 2/2003 | Mantius et al. | 426/488 |
| 2003/0119825 A1 | 6/2003 | Folger et al. | 514/226.5 |
| 2003/0170289 A1 | 9/2003 | Chen et al. | 424/426 |
| 2003/0191157 A1 | 10/2003 | Doen et al. | 514/337 |
| 2004/0142043 A1 | 7/2004 | Maeda et al. | 524/499 |
| 2004/0176341 A1 | 9/2004 | Chou et al. | 514/179 |
| 2005/0019436 A1 | 1/2005 | Burch et al. | 424/760 |
| 2005/0069591 A1 | 3/2005 | Bernstein et al. | 424/489 |
| 2005/0240166 A1 | 10/2005 | Hamer et al. | 604/890.1 |
| 2006/0160823 A1 | 7/2006 | Witchey-Lakshmanan et al. 514/254.07 | |
| 2006/0211982 A1 | 9/2006 | Prestrelski et al. | 604/60 |
| 2007/0196416 A1 | 8/2007 | Li et al. | 424/422 |
| 2008/0096967 A1 | 4/2008 | Lopez et al. | 514/567 |
| 2008/0132493 A1 | 6/2008 | Folger et al. | 514/224 |
| 2008/0145383 A1 | 6/2008 | Zauner et al. | 424/208.1 |
| 2008/0160067 A1 | 7/2008 | Boeckh et al. | 424/441 |
| 2008/0200383 A1 | 8/2008 | Jennings et al. | 514/11.3 |
| 2008/0220069 A1 | 9/2008 | Allison | 424/489 |
| 2008/0226689 A1 | 9/2008 | Berry et al. | 424/423 |
| 2008/0248999 A1 | 10/2008 | Steiner | 514/1.1 |
| 2008/0260840 A1 | 10/2008 | Alessi et al. | 514/12 |
| 2008/0305161 A1 | 12/2008 | Shah et al. | 424/456 |
| 2009/0143737 A1 | 6/2009 | Kobayashi et al. | 604/164.08 |
| 2009/0215883 A1 | 8/2009 | Bouzada et al. | 514/449 |
| 2009/0226530 A1 | 9/2009 | Lassner et al. | 514/1.1 |
| 2009/0233912 A1 | 9/2009 | Castile et al. | 514/220 |
| 2010/0098735 A1 | 4/2010 | Jain et al. | 424/422 |
| 2010/0120660 A1 | 5/2010 | Balschmidt et al. | 514/1.1 |
| 2011/0230569 A1 | 9/2011 | Nistor et al. | 514/777 |
| 2012/0046625 A1 | 2/2012 | Prestrelski et al. | 514/6.8 |
| 2012/0232001 A1 | 9/2012 | Prestrelski et al. | 514/5.9 |
| 2013/0123739 A1 | 5/2013 | Yoshikawa | 604/408 |
| 2013/0317477 A1 | 11/2013 | Edwards et al. | |
| 2014/0058337 A1 | 2/2014 | Claussen et al. | 604/260 |
| 2014/0171362 A1 | 6/2014 | Prestrelski et al. | 514/5.9 |
| 2014/0179599 A1 | 6/2014 | Prestrelski et al. | 514/6.8 |
| 2014/0179600 A1 | 6/2014 | Prestrelski et al. | 514/6.8 |
| 2014/0221288 A1 | 8/2014 | Prestrelski et al. | 514/7.2 |
| 2015/0250855 A1 | 9/2015 | Prestrelski et al. | 514/6.8 |

FOREIGN PATENT DOCUMENTS

| | | |
|---|---|---|
| CN | 102164579 | 8/2011 |
| CN | 103442695 | 9/2012 |
| EP | 0 916 347 | 5/1999 |
| EP | 1 502 589 | 2/2005 |
| EP | 2 060 268 | 5/2009 |
| EP | 2526996 | 11/2012 |
| GB | 2 119 248 | 11/1983 |
| JP | H07-506287 | 7/1995 |
| JP | H05-507085 | 10/1997 |
| JP | 2006-506363 | 2/2006 |
| JP | 2006-511582 | 4/2006 |
| JP | 2007-537283 | 12/2007 |
| JP | 2008-543857 | 12/2008 |
| JP | 2009-523798 | 6/2009 |
| JP | 2010-537963 | 12/2010 |
| JP | 2011-507843 | 3/2011 |
| JP | 2011-520875 | 7/2011 |
| JP | 2014-507484 | 3/2014 |
| JP | 2014-510077 | 4/2014 |
| WO | WO 91/16882 | 11/1991 |
| WO | WO 94/13344 | 6/1994 |
| WO | WO 95/32730 | 12/1995 |
| WO | WO 96/009814 | 4/1996 |
| WO | WO 98/009613 | 3/1998 |
| WO | WO 98/016250 | 4/1998 |
| WO | WO 98/027963 | 7/1998 |
| WO | WO 00/016829 | 3/2000 |
| WO | WO 01/076682 | 10/2001 |
| WO | WO 01/078687 | 10/2001 |
| WO | WO 02/000137 | 1/2002 |
| WO | WO 02/049660 | 6/2002 |
| WO | WO 03/007782 | 1/2003 |
| WO | WO 03/041684 | 5/2003 |
| WO | WO 03/051398 | 6/2003 |
| WO | WO 2004/035601 | 4/2004 |
| WO | WO 2004/037242 | 5/2004 |
| WO | WO 2004/057939 | 7/2004 |
| WO | WO 2004/057959 | 7/2004 |
| WO | WO 2004/091666 | 10/2004 |
| WO | WO 2004/098643 | 11/2004 |
| WO | WO 2005/010079 | 2/2005 |
| WO | WO 2006/031376 | 3/2006 |
| WO | WO 2006/110551 | 10/2006 |
| WO | WO 2006/138347 | 12/2006 |
| WO | WO 2007/140312 | 12/2007 |
| WO | WO 2008/030469 | 3/2008 |
| WO | WO 2008/041245 | 4/2008 |
| WO | WO 2008/098212 | 8/2008 |
| WO | WO 2008/132224 | 11/2008 |
| WO | WO 2009/027697 | 3/2009 |
| WO | WO 2009/045837 | 4/2009 |
| WO | WO 2009/060473 | 5/2009 |
| WO | WO 2009/070298 | 6/2009 |
| WO | WO 2009/082437 | 7/2009 |
| WO | WO 2010/018596 | 2/2010 |
| WO | WO 2010/024209 | 3/2010 |
| WO | WO 2011/060908 | 5/2011 |
| WO | WO 2011/154725 | 12/2011 |
| WO | WO 2012/012460 | 1/2012 |
| WO | WO 2012/122535 | 9/2012 |
| WO | WO 2013/067022 | 5/2013 |
| WO | WO 2013/173687 | 11/2013 |
| WO | WO 2014/036323 | 3/2014 |
| WO | WO 2015/120231 | 8/2015 |
| WO | WO 2015/153728 | 10/2015 |

OTHER PUBLICATIONS

Preservatives in Natural Products: Benzyl Alcohol, from https://naturespulchritude.wordpress.com/2014/05/06/preservatives-in-natural-products-benzyl-alcohol/, May 6, 2014, pp. 1-4.*

Mannitol, from https://pubchem.ncbi.nlm.nih.gov/compound/D-mannitol#section=Top, accessed Jul. 16, 2018, pp. 1-2.*

Office Action issued in European Application No. 15706976.6, dated Mar. 8, 2018.

Administer Intramuscular, Subcutaneous, and Intradermal Injections, from http://www.brooksidepress.org/Products/Administer_IM_SQ_and_ID_Injections/lesson_1 . . . , pp. 1-3, published on 2007.

Amylin Agonists, from http://www.globalrph.com/amylin-agonists.htm, pp. 1-5, accessed Nov. 30, 2014.

Anderson et al., "Revised estimate of the prevalence of multiple sclerosis in the United States", Ann. Neruol, 31(3):333-336, 1992.

Amon and Aharoni, "Neurogenesis and neuroprotection in the CNS—fundamental elements in the effect of Glatiramer acetate on treatment of autoimmune neurological disorders", Mol. Neurobiol., 36:245-253, 2007.

Autret, E. et al.: "Double-blind, randomized trial of diazepam versus placebo for prevention of recurrence of febrile seizures", The Journal of Pediatrics, vol. 117, No. 3, Sep. 1990, p. 490-494.

Bjartmar and Fox, "Pathological mechanisms and disease progression of multiple sclerosis: therapeutic implications", Drugs of Today, 38:17-29, 2002.

Bornstein et al., "A pilot trial of Cop 1 in exacerbateing remitting multiple sclerosis", New Eng. J. Med., 317:408-414,1987.

(56) References Cited

OTHER PUBLICATIONS

Bornstein et al., "A placebo-controlled, double-blind, randomized, two-center, pilot trial of Cop-1 in chronic progressive multiple sclerosis", Neurology, 41:533-539, 1991.
Bromberg, L. et al., "Transport of proteins dissolved in organic solvents across biomimetic membranes", Proceedings of the National Academy of Sciences 92(5):1262-1266, 1995.
Brown: "Clinicians' Guide to Diabetes Gadgets and Gizmos", Clinical Diabetes, 2008, 26, pp. 66-71.
Buffer Reference Center, from http://sigmaaldrich.com/life-science/core-bioreagents/biological-buffers/learningcenter. Accessed Jul. 3, 2013.
Carpenter, et al., "Rational Design of Stable Lyophilized Protein Formulations: Theory and Practice." pp. 1-25. 2002.
Cervera et al., "Mechanism of action of exenatide to reduce postprandial hyperglycemia in type 2 diabetes", Am J Physiol Endoclinol Metab 294: E846-E852, 2008.
Chang and Hershenson, "Practical Approaches to Protein Formulation Development", In: Rationale Design of stable protein formulations-theory and practice, pp. 1-25, 2002.
Chang et al., "Development of stable freeze-dried formulation of recombinant human interleukin-1 receptor antagonist", Pharm. Res., 13(2):243-249, 1996.
Citric Acid, from http://www.boldsky.com/health/nutrition/2011/natural-citric-acid-sources-030811.html, pp. 1-3, accessed Nov. 26, 2014.
Comi & Filippi, "Treatment with glatiramer acetate delays conversion to clinically definiate multiple sclerosis (CDMS) in patients with clinically isolated syndromes (CIS)", Neurology, 71(2):153, 2008.
Comi et al, "Results from a phase III, one-year, randomized, double-blind, parallel-group, dosecomparison study with glatiramer acetate in relapsing-remitting multiple sclerosis", Mult. Sclerosis., 14(suppl. 1):S299-S301, 2008.
Comi et al., "European/Canadian multicener, double-blind, randomized, placebo-controlled study of the effects of glatiramer acetate on magnetic resonance imaging-measured disease activity and burden in patents with relapsing multiple sclerosis", Ann. Neurol., 49:290-297, 2001.
Compston et al., "The Story of Multiple Sclerosis" In: McAlpine's Multiple Sclerosis. London: Churchill Livingston, pp. 3-42, 2006.
Definition of analog, from http://cancerweb.ncl.ac.uk/cgi-bin/omd?query=analog, pp. 1-5, accessed Jul. 7, 2005.
Definition of mimetic, from http://www.merriam-webster.com/medical/mimetic, p. 1, accessed Jun. 26, 2014.
DeLuca, "Freeze drying of pharmaceuticals", J. Vac. Sci. Technol., 14(1):620, 1977.
Dhib-Jalbut, "Glatirmaer acetate (Copaxone) therapy for multiple sclerosis", Pharmacol Ther., 98:245-255 2003.
Dhib-Jalbut, "Mechanisms of action of interferons and glatiramer acetate in multiple sclerosis", Neurology, 25 58(Suppl 4):S3-S9, 2002.
Diabetes Mellitus-Merck Manual, from http://www.merckmanuals.com/professional/print!endocrine_and_metabolic_disorders/diab . . . , pp. 1-22, accessed Apr. 2, 2013.
DMSO Facts, from http://www.theundergroundcure.com/dmso-facts.html, p. 1, accessed Nov. 26, 2014.
Engeloch et al: "Stability of Screening Compounds in Wet DMSO", Journal of Biomolecular Screening, 2008, 13, pp. 999-1006.
European Search Report for EP Appl. No. EP 12180169.0 dated Oct. 25, 2012.
Fleming and Carrithers, "Diagnosis and management of multiple sclerosis", Professional communications, Inc., 4 pages, 2002.
Geary et al., "Pancreatic Glucagon Fails to Inhibit Sham Feeding in The Rat", Peptides, vol. 1, 163-166, 1982.
Glossary of medical education terms, Institute of International Medical Education. http://www.iime.org/glossary.htm. Accessed in Mar. 2013.
Guideline on clinical investigation of medicinal products for the treatment of multiple sclerosis EMEA, London Sep. 16, 2006.
Human insulin, from http://www.ncbi.nlm.nih.gov/protein/AAA59172.1, p. 1, accessed Nov. 26, 2014.
Hypoglycemia-Merck Manual, from http://web.archive.org/web/20120115004118/http://www.merckmanuals.com/professional/ pp. 1-2, published on May 2007.
Iasemidis LD, "Epileptic Seizure Prediction and Control." IEEE Transac Biomed Eng. 50:549-558. 2003.
International Search Report and Written Opinion issued in PCT Application PCT/US2012/062816, dated Jan. 31, 2013.
International Search Report and Written Opinion issued in PCT Application PCT/US2013/048293, dated Aug. 8, 2013.
International Search Report and Written Opinion issued in PCT Application PCT/US2011/044576, dated Dec. 14, 2011.
International Search Report and Written Opinion issued in PCT Application PCT/US2012/028621, dated Aug. 22, 2012.
International Search Report and Written Opinion Issued in PCT Application No. PCT/US2014/015123, dated Apr. 3, 2014.
International Search Report and Written Opinion issued in PCT/US2015/044060, dated Nov. 2, 2015.
International Search Report and Written Opinion issued in PCT/US2015/014756, dated Sep. 25, 2015.
International Search Report and Written Opinion issued in PCT/US2015/023820, dated Jun. 18, 2015. (Attorney Docket No. Xerp.P0009WO).
Johnson et al., "Extended use of glatiramer acetate (Copaxone) is well its tolerated and maintains its clinical effect on multiple sclerosis relapse rate and degree of disability", Neurology, 50:701-708, 1998.
Kansara et al., "Subcutaneous delivery", Drug. Deliv. Technol, 9(6):38-42, 2009.
Knudsen, F Ursin; "Recurrence risk after first febrile seizure and effect of short term diazepam prophylaxis", Archives of Disease in Childhood, vol. 60, 1985 p. 1045-1049.
Izutsu, Stabilization of Therapeutic Proteins by Chemical and Physical Methods, pp. 287-292, from Therapeutic Proteins Methods and Protocols, Edited by C. Mark Smales and David C. James, published on 2005.
Meyer et al., "Preparation and in Vitro characterization of gentamycin-impregnated biodegradable beads suitable for treatment of osteomyelitis", Journal of Pharmaceutical Sciences, 87(9): 1149-1154, 1998.
Nash, "Suspensions", Encyclopedia of Pharmaceutical Technology, 6:3597-3610, 2007.
Noseworthy et al, "Multiple sclerosis", New Engl. J. Med., 343:938-952, 2000.
Pellock, John et al.: Pediatric Epilepsy: Diagnosis and Therapy: Third Edition—Chapter 19 "Febrile Seizures", 2008, p. 293-301.
Rubino, Solubilization of Some Poorly Soluble Drugs by Cosolvents, PhD dissertation, The University of Arizona, 1984.
Ruggiere et al., "Glatiramer acetate in multiple sclerosis: A review", CNS Drug Reviews, 13(2):178-191, 2007.
Shire et al., "Challenges in the development of high protein concentration formulations", J. Pharm. Sci., 93(6):1390-1402, 2004.
Tselis et al., "Glatiramer acetate in the treatment of multiple sclerosis", Neuropsychiatric Dis. Treat. 5Q, 3(2):259-267, 2007.
Vanderweele et al., "Glucagon, Satiety From Feeding and Liver/Pancreatic Interactions," Brain Research Bulletin, 17:539-543 (1986).
Wang, "Lyophilization and development of solid protein pharmaceuticals", Int. J. Pharm., 203(1-2):1-60, 2000.
Water, from http://www.biology-online.org/dictionary/Water, pp. 1-3, accessed Apr. 24, 2014.
Weber et al., "Mechanism of action of glatiramer acetate in treatment of multiple sclerosis", Neurotherapeutics, 4(4):647-653, 2007.
Williams and Polli, "The lyophilization of pharmaceuticals: a literature review", Journal of Parenteral Science and Technology, 38(2), 1984.
Wolinsky et al, "Glatiramer acetate in primary progressive multiple sclerosis: Results of a multinationa, multicener, double-blind, placebo-controlled trial", Ann Neurool, 61:14-24, 2007.
Wolinsky, "The use of glatiramer acetate in the treatment of multiple sclerosis", Adv. Neurol., pp. 273-292, 2006.

(56) References Cited

OTHER PUBLICATIONS

Zacharis et al., "Volatile buffers can override the 'pH memory' of subtilisin catalysis in organic media", Proc. Natl. Acad. Sci. USA, 96(4):1201-1205, 1999.

Ziemssen and Schrempf, "Glatiramer acetate: Mechanisms of action in multiple sclerosis", International Rev. of Neurobiol., 79:537-570, 2007.

Hyrdochloric Acid, from http://peoplesrx.com/hyrodchloric-acid-and-the-bodys-primary-digestant/, pp. 1-2, accessed Jun. 23, 2016.

Naturally-occurring amino acids, from http://www.benjamin-mills.com/chemistry/amino-acids.htm pp. 1-5 , accessed Jun. 23, 2016.

Richards et al. "Trehalose: a review of properties, history and human tolerance, and results of multiple safetX studies," *Food and Chemical Toxicology* 40: 871-898. 2002.

Griebel et al.: "SL651498, a GABAA Receptor Agonist with Subtype-Selective Efficacy, as a Potential Treatment for Generalized Anxiety Disorder and Muscle Spasms," CNS Drug Reviews, vol. p, No. 1, pp. 3-20, 2003.

International Search Report for PCT/US2016/053628, dated Feb. 9, 2017.

Edited by Katsuharu Kato, Medical English-Japanese Dictionary, B6 size, 11$^{th}$ edition, 3$^{rd}$ issue, Nanzando, 2002, p. 1082.

Extended European Search Report issued in European Application No. 17151475.5, dated Sep. 4, 2017.

International Preliminary Report on Patentability and Written Opinion issued in International Patent Application No. PCT/US2016/036921, dated Dec. 12, 2017.

International Preliminary Report on Patentability issued in International Application No. PCT/US2016/035792, dated Dec. 14, 2017.

International Preliminary Report on Patentability issued in International Application No. PCT/US2016/053628, dated Jan. 3, 2018.

Notice of Reasons for Rejection issued in Japanese Application No. 2015-520527, dated Nov. 30, 2017.

Office Action issued in Australian Application No 2017200295, dated Nov. 30, 2017.

Office Action issued in European Application No. 15750582.7 , dated Feb. 2, 2018.

Office Action issued in Indonesian Patent Application No. P-00201403186, dated Oct. 17, 2017.

Office Action issued in Israeli Application No. 228348, dated Oct. 29, 2017.

Office Action issued in Israeli Application No. 2363 93, dated Jul. 12, 2017.

Office Action issued in Thai Patent Application No. 140102311, dated Nov. 2, 2017.

Written Opinion issued in International Application No. PCT/US2016/053628, dated Sep. 28, 2017.

Office Action issued in Japanese Patent Application No. 2017-506262, dated Mar. 4, 2019.

Office Action issued in Chinese Patent Application No. 201580018099, dated Jan. 3, 2019.

Office Action issued in European Patent Application No. 17151475.5, dated Jul. 2, 2018, received Jul. 4, 2018.

Office Action issued in Indian Patent Application No. 10985/DELNP/2014, dated Aug. 17, 2018.

Office Action issued in Japanese Patent Application No. 2016-550716, dated Sep. 28, 2018.

Office Action issued in Canadian Patent Application No. 2,829,400, dated Mar. 20, 2018.

Office Action issued in Chinese Patent Application No. 201610221799.6, dated May 3, 2018.

Office Action issued in Indian Patent Application No. 3948/DELNP/2014, dated Apr. 26, 2018.

Office action issued in United Arab Emirates Patent Application No. 960/2013, dated Mar. 12, 2018.

\* cited by examiner

METHODS FOR PRODUCING STABLE THERAPEUTIC FORMULATIONS IN APROTIC POLAR SOLVENTS

CROSS REFERENCE TO RELATED APPLICATIONS

This application is a continuation of U.S. application Ser. No. 15/136,650, filed Apr. 22, 2016, now U.S. Pat. No. 9,649,364 which claims the benefit of U.S. Provisional Patent Application Ser. No. 62/233,032, filed Sep. 25, 2015, which is incorporated herein by reference in its entirety.

BACKGROUND OF THE INVENTION

A. Field of the Invention

The present invention relates generally to therapeutic formulations for parenteral administration. In particular, the invention concerns the use of aprotic polar solvents to prepare stable therapeutic formulations by dissolving a therapeutic agent (active ingredient) in an aprotic polar solvent system without the need for drying the peptide from a buffered aqueous solution prior to dissolution in the aprotic polar solvent system. In addition to the active ingredient, a stabilizing excipient(s) may also be included in the formulation, in particular an ionization stabilizing excipient.

B. Description of Related Art

Peptides dissolved in aprotic polar solvents can exhibit enhanced stability and solubility relative to aqueous solutions (see US 2014/0005135 and U.S. Pat. No. 8,697,644); however, direct dissolution of some peptides in an aprotic polar solvent is often not a viable method for preparing a stable and therapeutic composition due to the lack of storage stability. One particular example is glucagon, a 29-amino acid residue peptide hormone used for the treatment of hypoglycemia. Glucagon has an isoelectric point of approximately 7.0, and the molecule is essentially insoluble at neutral pH. Therefore, aqueous solutions must be made either acidic or alkaline before the molecule can be solubilized at therapeutically relevant concentrations. However, acidic and alkaline solutions promote glucagon degradation pathways, and the glucagon molecule has a well-known tendency to fibrillate and form gel-like aggregates in dilute acidic solutions. Therefore, due to the instability of the glucagon molecule, currently available therapeutics are sold as a lyophilized powder that must be reconstituted using a diluent immediately prior to use. By contrast, the glucagon molecule may exhibit enhanced stability and solubility in aprotic polar solvents, such as dimethyl sulfoxide (DMSO).

In addition to peptides and proteins, aprotic polar solvents can also enhance the solubility and stability of therapeutic small molecule drugs relative to aqueous solutions. For example, the small molecule drug diazepam exhibits extremely low solubility in water at neutral pH (<2 mg/mL). To enhance the solubility of diazepam the pH of the aqueous solution is made acidic or alkaline, which in turn increases the rate of hydrolysis and degradation. In contrast, diazepam is very soluble in the aprotic polar solvents dimethyl sulfoxide (DMSO) and n-methyl pyrrolidone (NMP), with a solubility at least an order of magnitude greater in DMSO and NMP relative to neutral water (>50 mg/mL). Additionally, in the absence of formulation excipients, the diazepam molecule is stable in DMSO and NMP, exhibiting stability for at least 6 months in the aprotic polar solvents under accelerated storage conditions (40° C., 75% RH) (see U.S. Pat. No. 9,125,805).

The preparation of non-aqueous peptide formulations via direct dissolution of a peptide in an aprotic polar solvent has been described in the prior art. For example, McMullen (GB Patent Application 2,119,248 A, hereinafter McMullen '248) describes the preparation of insulin solutions by directly dissolving insulin crystals in DMSO. Stevenson et al. (U.S. Pat. No. 5,932,547, hereinafter Stevenson '547), discloses peptide compositions prepared by directly dissolving the peptide in an aprotic polar solvent, such as DMSO or dimethylformamide (DMF). The compositions described by Stevenson '547 are solutions prepared by direct dissolution of the peptide powder as received from a manufacturer or supplier in the non-aqueous solvent, and do not include the use of stabilizing excipients added to the formulation to establish an acceptable ionization profile for preventing physical and/or chemical degradation of the therapeutic molecule. While direct dissolution of a therapeutic molecule in aprotic polar solvents such as DMSO may improve solubility relative to water, the molecule still remains susceptible to multiple physical and chemical degradation pathways. Consequently, direct dissolution in an aprotic polar solvent system has been found to not be suitable pathway for preparing stable formulations of many therapeutic molecules. As an example, at therapeutically relevant concentrations (e.g., 5 mg/mL, or approximately 0.45% (w/w)), solutions prepared by direct dissolution of glucagon powder in DMSO may initially form clear, single-phase compositions, but will eventually form insoluble aggregates within 24 hours at room temperature. Accordingly, direct dissolution of some peptides in an aprotic polar solvent is not a viable method for preparing a stable therapeutic formulation.

The formulations of the present invention are also distinct from those described by Prestrelski et al. (U.S. Pat. No. 8,697,644, hereinafter Prestrelski '644), which discloses peptide formulations prepared by drying the active ingredient (e.g. peptide) from a buffered aqueous solution, and then reconstituting the peptide powder in an aprotic polar solvent. According to this method, the ionization profile that the molecule acquires in the buffered aqueous solution from which it was dried may be retained both in the powder and following dissolution in an aprotic polar solvent system. The ability of a peptide to retain its ionization profile in the dry state from the last aqueous solution from which it was dried is referred to as "pH memory." However, this approach requires a drying step prior to reconstitution in the aprotic polar solvent, such as freeze-drying or spray-drying, where stabilizing excipients will be required to protect the molecule from the stresses encountered during drying (e.g. thermal stress, mechanical stress, interfacial stress). Further, the addition of a drying step adds significant costs, both in terms of time and expense, to the product development pathway, as the operating parameters and formulation components required for drying the molecule must often be optimized for a particular therapeutic agent, while transfer from the lab-scale to large-scale manufacturing and processing requires further method development and optimization.

Therefore, there remains a need for a formulation platform that couples the stability and solubility provided by aprotic polar solvent systems, but which simplifies and/or expedites the product development pathway by removing the requirement for drying the therapeutic molecule from an aqueous solution prior to reconstitution in a biocompatible aprotic polar solvent system.

SUMMARY OF THE INVENTION

Therapeutic molecules typically require an optimal or beneficial ionization profile in order to exhibit prolonged stability when solubilized in an aprotic polar solvent system. The present invention is drawn to the unexpected discovery that an optimal or beneficial ionization profile of a therapeutic molecule may be obtained by direct dissolution of the therapeutic agent in an aprotic polar solvent system containing a specified concentration of at least one ionization stabilizing excipient. Certain embodiments of the present invention are directed to methods for preparing stable formulations containing at least one therapeutic molecule solubilized in an aprotic polar solvent system, without requiring the therapeutic molecule to be previously dried from a buffered aqueous solution prior to reconstitution in the aprotic polar solvent system.

The inventors have discovered a solution to address the problems of potential stability issues and added manufacturing complexity that can occur when therapeutic agents are directly dissolved in aprotic polar solvents or dried from an aqueous solution prior to being reconstituted in an aprotic polar solvent. The solution resides in directly dissolving the therapeutic agent (e.g. the powder as received from a commercial manufacturer or supplier) along with an effective amount of an ionization stabilizing excipient for establishing an appropriate ionization profile of the therapeutic agent in the aprotic polar solvent system.

In particular, the ability to circumvent the need for drying the peptide from a buffered aqueous solution, for example via lyophilization, prior to reconstitution in the aprotic polar solvent system is anticipated to save considerable time and cost throughout the various product development stages. It is well-known that the development of a drying method is an expensive and time-intensive processing step that often must be tailored to each therapeutic molecule. Further, during manufacturing the ability to scale-up the drying step is complicated by the use of equipment and/or instruments that differ considerably from those employed at the lab-scale, where the processing steps were initially studied and optimized. Accordingly, the ability to prepare a stable therapeutic peptide formulation via direct dissolution of the active ingredient in the aprotic polar solvent system, in the absence of such a drying step, will facilitate scale-up and manufacturing by eliminating a costly and time-consuming processing step. Further, during drying the therapeutic agent is exposed to multiple stresses than can degrade the molecule, and stabilizing excipients (e.g., disaccharides such as trehalose and sucrose) are often added to the formulation primarily to protect against degradation of the active agent during the drying process. By eliminating the drying step the use of additional stabilizing excipients, particularly those that are often included to provide stability during the drying step, may be minimized, thereby allowing for the overall formulation to be simplified.

An additional discovery by the inventors is that it is possible to prepare stable solutions of a therapeutic agent(s) solubilized in non-aqueous aprotic polar solvents (e.g. DMSO), by adding a specific amount of a compound, or combination of compounds, that function as an ionization stabilizing excipient. Without wishing to be bound by theory, it is believed that the ionization stabilizing excipient can act as a proton source (e.g., a molecule that can donate at least one proton to the therapeutic molecule) in the aprotic polar solvent system that may protonate the ionogenic groups on the therapeutic molecule such that the therapeutic molecule possesses an ionization profile having an improved physical and chemical stability in the aprotic polar solvent system. In one aspect of the present invention there is disclosed a stable formulation for parenteral injection. Alternatively, transdermal delivery such as through topical application to skin can be used.

Certain embodiments are directed to a formulation of a therapeutic agent comprising a therapeutic agent at a concentration of at least, at most, or about 0.1, 1, 10, 50, or 100 mg/mL to 150, 200, 300, 400, or 500 mg/ml or up to the solubility limit of the therapeutic agent in the aprotic polar solvent system comprising a concentration of at least one ionization stabilizing excipient that provides physical and chemical stability to the therapeutic agent. In certain aspects the therapeutic agent is a peptide. In further aspects the therapeutic agent is a small molecule. The formulation can comprise an ionization stabilizing excipient at a concentration of at least, at most, or about 0.01, 0.1, 0.5, 1, 10, or 50 mM to 10, 50, 75, 100, 500, 1000 mM, or up to the solubility limit of the ionization stabilizing excipient in the aprotic polar solvent system. In certain aspects the ionization stabilizing excipient concentration is between 0.1 mM to 100 mM. In certain embodiments the ionization stabilizing excipient may be a suitable mineral acid, such as hydrochloric acid. In certain aspects the ionization stabilizing excipient may be an organic acid, such as an amino acid, amino acid derivative, or the salt of an amino acid or amino acid derivative (examples include glycine, trimethylglycine (betaine), glycine hydrochloride, and trimethylglycine (betaine) hydrochloride). In a further aspect the amino acid can be glycine or the amino acid derivative trimethylglycine. In certain aspects a peptide is less than 150, 100, 75, 50, or 25 amino acids. In further aspects the aprotic solvent system comprises DMSO. The aprotic solvent can be deoxygenated, e.g., deoxygenated DMSO. In certain embodiments the formulation may be prepared by first adding the ionization stabilizing excipient to the aprotic polar solvent system, followed by addition of the therapeutic molecule. Alternatively, the therapeutic molecule may initially be solubilized in the aprotic polar solvent system followed by addition of the ionization stabilizing excipient. In a further aspect, the ionization stabilizing excipient and the therapeutic molecule may be solubilized simultaneously in the aprotic polar solvent system. In certain aspects the therapeutic agent is glucagon or salt thereof.

Other embodiments of the present invention are directed to methods of stably formulating a therapeutic agent (e.g., a peptide or a small molecule) comprising the steps of: (a) calculating or determining the appropriate ionization stabilizing excipient or proton concentration needed to achieve a stabilizing ionization profile of a target therapeutic agent (e.g., a peptide(s) or small molecule(s)) in an aprotic polar solvent system; (b) mixing at least one ionization stabilizing excipient with the aprotic polar solvent system to attain an appropriate ionization environment that provides the ionization profile determined in step (a); and (c) solubilizing the target therapeutic agent(s) in the aprotic solvent having an appropriate environment to physically and chemically stabilize the therapeutic agent. In certain non-limiting aspect the therapeutic agent is chemically or physically stable for at least or about 0.25, 0.5, 1, 2, 3, 4, or 5 years at room temperature. In certain aspects the dissolution of the therapeutic agent and the addition of the ionization stabilizing excipient to the aprotic polar solvent system can be done in any order or concurrently, thus the ionization stabilizing excipient can be mixed first followed by dissolution of the therapeutic agent, or the therapeutic agent can be dissolved followed by addition of the ionization stabilizing excipient to the solution, or the ionization stabilizing excipient and the therapeutic agent can be added or dissolved in an aprotic polar solvent system concurrently. In a further aspect the entire amount of a component (e.g., a therapeutic agent or an ionization stabilizing excipient) need not to be mixed at a particular point; that is, a portion of the one or more components can be mixed first, second, or concurrently, and another portion mixed at another time, first, second, or concurrently. In certain aspects the therapeutic agent can be a peptide, and the ionization stabilizing excipient may be a suitable mineral acid, such as hydrochloric acid. In certain aspects the peptide(s) is less than 150, 100, 75, 50, or 25 amino acids. The concentration of the therapeutic agent and/or ionization stabilizing excipient added to the solution can be between 0.01, 0.1, 1, 10, 100, 1000 mM to its solubility limit, including all values and ranges there between. In certain aspects the aprotic polar solvent system is deoxygenated. In a further aspect the aprotic polar solvent system comprises, consists essentially of, or consists of DMSO or deoxygenated DMSO.

In a further aspect of the present invention there is disclosed a method for treating or preventing a condition, disease, disorder, etc. comprising administering to a subject in need thereof a formulation(s) of the present invention in an amount effective to treat or prevent the condition, disease, disorder, etc. Any suitable dosage of a therapeutic agent (e.g., protein, peptide, or small molecule) may be administered in the methods of the present invention. The dosage administered will, of course, vary depending upon known factors, such as the pharmacodynamic characteristics of the particular compound, salt, or combination; the age, health, or weight of the subject; the nature and extent of symptoms; the metabolic characteristics of the drug and patient, the kind of concurrent treatment; the frequency of treatment; or the effect desired. In certain aspects hypoglycemia can be treated by administering a formulation described herein comprising an effective amount of glucagon.

The stable formulations described herein are useful for the parenteral injection of any therapeutic agent (protein, peptide, and/or small molecule) that has limited or poor stability or solubility in an aqueous environment. In certain aspects a formulation as described herein is provided in as an injectable formulation. The injectable formulation can be administered into the epidermal, dermal or subcutaneous layer of an animal. In certain aspects the formulations are administered intracutaneously.

Thus, in some embodiments, the therapeutic agent or peptide or salt thereof is selected from the group consisting of glucagon, pramlintide, insulin, leuprolide, an LHRH agonist, parathyroid hormone (PTH), amylin, botulinum toxin, hematide, angiotensin(1-7), an amyloid peptide, cholecystikinin, a conotoxin, a gastric inhibitory peptide, an insulin-like growth factor, a growth hormone releasing factor, an anti-microbial factor, glatiramer, glucagon-like peptide-1 (GLP-1), a GLP-1 agonist, exenatide, analogs thereof, and mixtures thereof. In a preferred embodiment, the peptide is glucagon or a glucagon analog or a glucagon peptidomimetic. In another embodiment, the peptide is parathyroid hormone. In yet another embodiment, the peptide is leuprolide. In still another embodiment, the peptide is glatiramer. In yet another embodiment, a first peptide is pramlintide and a second peptide is insulin. In still another embodiment, the first peptide is glucagon and the second peptide is exenatide.

Definitions

The term "dissolution" as used herein refers to a process by which a material(s) in a gas, solid, or liquid state becomes a solute(s), a dissolved component(s), of a solvent, forming a solution of the gas, liquid, or solid in the solvent. In certain aspects a therapeutic agent or an excipient, e.g., an ionization stabilizing excipient, is present in an amount up to its solubility limited or is fully solubilized. The term "dissolve" refers to a gas, liquid, or solid becoming incorporated into a solvent to form a solution.

The term "excipient" as used herein refers to a natural or synthetic substance formulated alongside the active or therapeutic ingredient (an ingredient that is not the active ingredient) of a medication, included for the purpose of stabilization, bulking, or to confer a therapeutic enhancement on the active ingredient in the final dosage form, such as facilitating drug absorption, reducing viscosity, enhancing solubility, adjusting tonicity, mitigating injection site discomfort, depressing the freezing point, or enhancing stability. Excipients can also be useful in the manufacturing process, to aid in the handling of the active substance concerned such as by facilitating powder flowability or non-stick properties, in addition to aiding in vitro stability such as prevention of denaturation or aggregation over the expected shelf life.

"Small molecule drugs" in the context of the present invention are biologically active compounds (and salts thereof) that can bring about a desired, beneficial, and/or pharmacological effect on a subject. These "small molecule drugs" are organic or inorganic compounds. Therefore, the small molecule drugs in the context of the present invention are not polymeric compounds. Typically, the small molecule drugs have a molecular weight of less than approximately 1000 Daltons. Certain small molecule drugs are "moisture sensitive" in that they are increasingly unstable in the presence of water. Also, salts that can be used with the small molecule drugs are known to those skilled in the art and include salts with inorganic acids, organic acids, inorganic bases, or organic bases.

The term "therapeutic agent" encompasses proteins, peptides, small molecule drugs, and pharmaceutically acceptable salts thereof. Useful salts are known to those skilled in the art and include salts with inorganic acids, organic acids, inorganic bases, or organic bases. Therapeutic agents useful in the present invention are those protein, peptide, and small molecule compounds that affect a desired, beneficial, and often pharmacological, effect upon administration to a human or an animal, whether alone or in combination with other pharmaceutical excipients or inert ingredients.

The term "peptide" and "peptide compound" refers to amino acid or amino acid-like (peptidomimetics) polymers of up to about 200 amino acid residues bound together by amide (CONH) or other linkages. In certain aspects a peptide can be up to 150, 100, 80, 60, 40, 20, or 10 amino acids. "Protein" and "protein compound" refer to polymers of greater than 200 amino acid residues bound together by amide linkages. Analogs, derivatives, agonists, antagonists, and pharmaceutically acceptable salts of any of the peptide or protein compounds disclosed here are included in these terms. The terms also include peptides, proteins, peptide compounds, and protein compounds that have D-amino acids, modified, derivatized, or naturally occurring amino acids in the D- or L-configuration and/or peptomimetic units as part of their structure.

"Analogue" and "analog," when referring to a peptide or protein, refers to a modified peptide or protein wherein one or more amino acid residues of the peptide or protein have been substituted by other amino acid residues, or wherein one or more amino acid residues have been deleted from the peptide or protein, or wherein one or more amino acid residues have been added to the peptide or protein, or any combination of such modifications. Such addition, deletion, or substitution of amino acid residues can take place at any point, or multiple points, along the primary structure comprising the peptide, including at the N-terminal of the peptide or protein and/or at the C-terminal of the peptide or protein.

"Derivative," in relation to a parent peptide or protein, refers to a chemically modified parent peptide or protein or an analog thereof, wherein at least one substituent is not present in the parent peptide or protein an analog thereof. One such non-limiting example is a parent peptide or protein which has been covalently modified. Typical modifications are amides, carbohydrates, polysaccharides, glycans, alkyl groups, acyl groups, esters, pegylations and the like.

"Single-phase solution" refers to a solution prepared from a therapeutic agent that is dissolved in a solvent, or solvent system (e.g., mixture of two or more solvents), wherein the therapeutic agent is completely dissolved in the solvent and there is no longer particulate matter visible, such that the solution can be described as optically clear. A single-phase solution may also be referred to as a "single-phase system," and is distinguished from a "two-phase system" in that the latter is comprised of particulate matter (e.g. powder) suspended in a fluid.

"Inhibiting" or "reducing" or any variation of these terms includes any measurable decrease or complete inhibition to achieve a desired result.

"Effective" or "treating" or "preventing" or any variation of these terms means adequate to accomplish a desired, expected, or intended result.

"Chemical stability," when referring to a therapeutic agent, refers to an acceptable percentage of degradation products produced by chemical pathways such as oxidation and/or hydrolysis and/or fragmentation and/or other chemical degradation pathways. In particular, a formulation is considered chemically stable if no more than about 20% breakdown products are formed after one year of storage at the intended storage temperature of the product (e.g., room temperature); or storage of the product at 25° C./60% relative humidity for one year; or storage of the product at 40° C./75% relative humidity for one month, and preferably three months. In some embodiments, a chemically stable formulation has less than 20%, less than 15%, less than 10%, less than 5%, less than 4%, less than 3%, less than 2%, or less than 1% breakdown products formed after an extended period of storage at the intended storage temperature of the product.

"Physical stability," when referring to a therapeutic agent, refers to an acceptable percentage of aggregates (e.g., dimers, trimers and larger forms) being formed. In particular, a formulation is considered physically stable if no more that about 15% aggregates are formed after one year of storage at the intended storage temperature of the product (e.g., room temperature); or storage of the product at 25° C./60% relative humidity for one year; or storage of the product at 40° C./75% relative humidity for one month, and preferably three months. In some embodiments, a physically stable formulation has less than less than 15%, less than 10%, less than 5%, less than 4%, less than 3%, less than 2%, or less than 1% aggregates formed after an extended period of storage at the intended storage temperature of the product.

"Stable formulation" refers to a formulation where at least about 65% of the therapeutic agents (e.g., peptides or salts thereof) remain chemically and physically stable after two months of storage at room temperature. Particularly preferred formulations are those in which at least about 80%, 85%, 90%, 91%, 92%, 93%, 94%, 95%, 96%, 97%, 98%, or 99% chemically and physically stable therapeutic agent remains under these storage conditions. Especially preferred stable formulations are those which do not exhibit degradation after sterilizing irradiation (e.g., gamma, beta, or electron beam).

As used herein, "parenteral administration" refers to administration of a therapeutic agent to a patient via a route other than the alimentary canal—any administration that is not by way of the digestive tract.

As used herein, "parenteral injection" refers to the administration of therapeutic agents (e.g., peptides or small molecules) via injection under or through one or more layers of skin or mucus membranes of an animal, such as a human. Standard parenteral injections are given into the subcutaneous, intramuscular, or intradermal region of an animal, e.g., a human. These deep locations are targeted because the tissue expands more easily relative to shallow dermal sites to accommodate injection volumes required to deliver most therapeutic agents, e.g., 0.1 to 3.0 cc (mL).

The term "intracutaneous" encompasses administration into the epidermal, dermal or subcutaneous skin layer.

As used herein, the term "aprotic polar solvent" refers to a polar solvent which does not contain acidic hydrogen and thus does not act as a hydrogen bond donor. Polar aprotic solvents include, but are not limited to dimethylsulfoxide (DMSO), dimethylformamide (DMF), ethyl acetate, n-methyl pyrrolidone (NMP), dimethylacetamide (DMA), and propylene carbonate.

As used herein, the term "aprotic polar solvent system" refers to a solution wherein the solvent is a single aprotic polar solvent (for example, neat DMSO), or a mixture of two or more aprotic polar solvents (for example, a mixture of DMSO and NMP).

As used herein, "residual moisture" may refer to the residual moisture in the drug powder following preparation by the manufacturer/supplier. Typical powders often have residual moisture contents ranging from up to 10% (w/w). When these powders are dissolved in an aprotic polar solvent system, the residual moisture in the powder is incorporated into the formulation. Additionally, the aprotic polar solvents may also contain a certain level of residual moisture. For example, a freshly opened bottle of USP-grade DMSO typically contains up to 0.1% (w/w) moisture. The residual moisture is different from "added moisture," where water is intentionally added to the formulation, for example to serve as a co-solvent, or to depress the freezing point of the aprotic polar solvent system. Moisture may also be introduced into the formulation during addition of an ionization stabilizing excipient (for example, through addition of a mineral acid from an aqueous stock solution (e.g. 1 N HCl)). The total moisture content (% w/w, unless otherwise stated) in a formulation immediately following preparation is due to the contributions from both the residual moisture and the added moisture.

The term "about" or "approximately" or "substantially unchanged" are defined as being close to as understood by one of ordinary skill in the art, and in one non-limiting embodiment the terms are defined to be within 10%, preferably within 5%, more preferably within 1%, and most preferably within 0.5%. Further, "substantially non-aqueous" refers to less than 5%, 4%, 3%, 2%, 1%, or less by weight or volume of water.

"Pharmaceutically acceptable" ingredient, excipient or component is one that is suitable for use with humans and/or animals without undue adverse side effects (such as toxicity, irritation and allergic response) commensurate with a reasonable benefit/risk ratio.

"Pharmaceutically acceptable carrier" means a pharmaceutically acceptable solvent, suspending agent, or vehicle for delivering a drug compound of the present invention to a mammal such as a human.

As used herein an "ionization stabilizing excipient" is an excipient that establishes and/or maintains a particular ionization state for a therapeutic agent. In certain aspects the ionization stabilizing excipient can be, or includes, a molecule that donates at least one proton under appropriate conditions or is a proton source. According to the Bronsted-Lowry definition, an acid is a molecule that can donate a proton to another molecule, which by accepting the donated proton may thus be classified as a base. As used in this application, and as will be understood by the skilled technician, the term "proton" refers to the hydrogen ion, hydrogen cation, or $H^+$. The hydrogen ion has no electrons and is composed of a nucleus that typically consists solely of a proton (for the most common hydrogen isotope, protium). Specifically, a molecule that can donate at least one proton to the therapeutic agent is considered an acid or proton source, regardless of whether it is completely ionized, mostly ionized, partially ionized, mostly unionized, or completely unionized in the aprotic polar solvent.

As used herein a "mineral acid" is an acid that is derived from one or more inorganic compounds. Accordingly, mineral acids may also be referred to as "inorganic acids." Mineral acids may be monoprotic or polyprotic (e.g. diprotic, triprotic, etc.). Examples of mineral acids include hydrochloric acid (HCl) and phosphoric acid ($H_3PO_4$).

As used herein an "organic acid" is an organic compound with acidic properties (i.e. can function as a proton source). Carboxylic acids are one example of organic acids. Other known examples of organic acids include, but are not limited to, alcohols, thiols, enols, phenols, and sulfonic acids. Organic acids may be monoprotic or polyprotic (e.g. diprotic, triprotic, etc.)

"Charge profile," "charge state," "ionization," "ionization state," and "ionization profile" may be used interchangeably and refer to the ionization state due to protonation and/or deprotonation of the peptide's ionogenic groups.

As used herein, a "co-formulation" is a formulation that contains two or more therapeutic agents dissolved in an aprotic polar solvent system. The therapeutic agents may belong to the same class (for example, a co-formulation comprising two or more therapeutic peptides, such as insulin and pramlintide), or the therapeutic agents may belong to different classes (for example a co-formulation comprising one or more therapeutic small molecules and one or more therapeutic peptide molecules, such as GLP-1 and lisofylline).

The use of the word "a" or "an" when used in conjunction with the term "comprising" in the claims and/or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DETAILED DESCRIPTION OF THE INVENTION

Figure 1:
FIG. 1 (left image) shows the formation of insoluble particles when glucagon is directly dissolved in DMSO at 5 mg/mL (as described by Stevenson '547) following 24 hours at room temperature. The image on the right shows a formulation prepared by solubilizing glucagon in DMSO (at 5 mg/mL concentration) with 5 mM glycine hydrochloride, which remained clear following at least six weeks storage at 40° C.

When prepared as aqueous solutions, standard small molecule, peptide, and protein molecules may be susceptible to multiple physical and chemical degradative pathways. For many of these therapeutic molecules, degradation pathways that require water (e.g. hydrolysis, racemization, deamidation) cannot be avoided and consequently the molecule cannot be adequately stabilized. Accordingly, many therapeutic agents cannot be prepared as stable solutions for parenteral injection, and are instead prepared as powders that are reconstituted immediately prior to use.

To address the physical and/or chemical instability that many therapeutic molecules exhibit in water, formulations may be prepared wherein the therapeutic agent is dissolved in a biocompatible non-aqueous liquid, such as an aprotic polar solvent. Examples from the prior art were described above, particularly Stevenson '547 which discloses compositions prepared by direct dissolution of a peptide powder in an aprotic polar solvent, and Prestrelski '644 which discloses drying the peptide powder from a buffered aqueous solution prior to dissolution in DMSO.

The use of aprotic polar solvents to prepare non-aqueous therapeutic formulations to inhibit many common degradation pathways, particularly those involving water, can significantly improve the stability of the solubilized or dissolved therapeutic molecule(s). However, problems still remain with the compositions and methods disclosed in the prior art. In particular, direct dissolution of a therapeutic molecule in an aprotic polar solvent is not a suitable approach for preparing stable compositions of most therapeutic molecules; dissolution of leuprolide described in Stevenson '547 is an exception. As noted previously, and as will be furthered detailed in the examples below, when solubilized directly in DMSO at a concentration of 5 mg/mL the peptide hormone glucagon will form insoluble aggregates within one day of storage at room temperature. For a composition comprising only glucagon and DMSO, 5 mg/mL corresponds to approximately 0.45% (w/w) of the peptide compound, indicating that at even relatively low concentrations, direct dissolution in an aprotic polar solvent system is by itself incapable of preventing physical aggregation and/or gelation of a therapeutic molecule. Moreover, therapeutic molecules that may not form insoluble aggregates in an aprotic polar solvent system may nonetheless be prone to chemical degradation when solubilized directly in an aprotic polar solvent system.

Without wishing to be bound by theory, it is thought that in order to exhibit enhanced or optimal stability and solubility when formulated in an aprotic polar solvent system, a therapeutic molecule may require a specific ionization profile. The ionization profile is the charge state acquired via protonation and/or deprotonation of the therapeutic molecule's ionogenic groups. For example, protonation of the ionogenic amino acid residues (e.g. arginine, lysine) comprising a therapeutic peptide will confer an overall positive charge on the molecules in solution. The relatively long-range electrostatic repulsions between positively charged peptide molecules may inhibit the short-range hydrophobic interactions that can result in physical aggregation and/or gelation. Thus, in the absence of sufficient protonation (i.e., an optimal or beneficial ionization profile), therapeutic molecules dissolved in an aprotic polar solvent system may be physically unstable and lead to the formation of soluble and/or insoluble aggregates. Accordingly, it may be necessary to include at least one excipient in a sufficient concentration to function as an ionization stabilizing agent that is capable of imparting the ionization profile for improved physical and/or chemical stability to the active agent in the aprotic polar solvent system. As will be explained in the following sections, and illustrated by way of several examples, the appropriate concentration of the ionization stabilizing excipient(s) that must be added to the solution depends on several factors including, but not limited to, the chemical structure of the ionization stabilizing excipient, the chemical structure of the active agent(s), the concentration of the active(s), the solvent system used, the presence of co-solvents, and the presence of additional excipients or formulation components and their respective concentrations.

The compositions and methods disclosed by Prestrelski '644 are designed to establish an optimal ionization profile for therapeutic molecules before they are solubilized in an aprotic polar solvent system. As disclosed by Prestrelski '644, a peptide powder from a supplier/manufacturer is initially dissolved in a buffered aqueous solution where the pH of the buffered aqueous peptide solution is set to that of optimal stability and solubility for the specific peptide. The peptide is then dried (for example via freeze drying or spray drying) to a powder from the aqueous solution such that the ionization profile of the peptide molecule in the powder may be about equal to the ionization profile of the peptide molecule in the aqueous solution from which it was dried. When the peptide powder is then solubilized in an aprotic polar solvent system, the ionization profile of the peptide molecule may be about equal to the ionization profile of the peptide molecule in the powder. Accordingly, the ionization profile of the peptide molecule in the aprotic polar solvent system is about equal to the ionization profile of the peptide molecule in the buffered aqueous solution.

The formulation approach disclosed by Prestrelski '644 (which is termed "pH memory" in the '644 patent) can overcome the stability issues (i.e., physical and chemical degradation) encountered when a therapeutic molecule is directly dissolved in an aprotic polar solvent system. However, the requirement of drying the therapeutic molecule from a buffered aqueous solution in order to optimize the ionization profile of the molecule and impart pH memory before it is solubilized in an aprotic polar solvent imposes significant added costs, both in terms of time and expense, to the formulation development pathway. In particular, the drying process is well known to impose several stresses on the therapeutic molecule, and additional excipients (e.g., lyoprotectants such as trehalose and sucrose, and/or surfactants such as polysorbate 80) must be included in the aqueous solution in sufficient amounts to protect the therapeutic molecule, thereby increasing the cost and complexity of the formulation. Further, the drying process (e.g., spray drying, freeze drying) must often be optimized for a given therapeutic molecule, both at the lab-scale during initial research and development where the process is initially developed, and then during the manufacturing-scale as the process is scaled-up and transferred to instruments and facilities capable of producing commercial-scale batches. Consequently, the combination of initially developing and optimizing a drying process for a given therapeutic molecule, coupled with the time and costs associated with both transferring the method and incorporating an additional step in the manufacturing process can be very expensive. Thus, there is a need for a method of providing the therapeutic molecule(s) with an appropriate ionization profile in an aprotic polar solvent system without the requirement of drying the molecule from a buffered aqueous solution where the pH of the aqueous solution is set to provide an appropriate ionization profile for the molecule.

The inventors have provided a solution that provides the increased stability and solubility exhibited by many therapeutic molecules in aprotic polar solvents when they possess an appropriate or optimal ionization profile, but without having to dry the powder from an aqueous solution prior to dissolution in an aprotic polar solvent system. The solution resides in dissolving an ionization stabilizing excipient(s) directly in the aprotic polar solvent, coupled with dissolution of the peptide molecule or small molecule directly in the aprotic polar solvent solution. Without wishing to be bound by theory, it is believed that by providing a sufficient quantity of ionization stabilizing excipient to achieve an appropriate or optimal ionization profile of the therapeutic molecule, electrostatic repulsion between therapeutic molecules possessing the same charge polarity (i.e. negatively or positively charged) may be sufficient in magnitude to prevent physical degradation (e.g., via short-range hydrophobic interaction between molecules that lead to aggregation). This is especially important for molecules that exhibit a tendency to aggregate in solution, particularly as the concentration of the molecule in solution is increased. Further, by controlling and optimizing the extent of the ionization (i.e., protonation or deprotonation) of the therapeutic agent, chemical degradation can be minimized, as, for example, an excess of protonation may promote chemical instability via degradative reactions such as oxidation (for example, oxidation of methionine residues) and fragmentation (for example, cleavage of the peptide backbone). Accordingly, for some therapeutic molecules there may be an optimal or beneficial ionization profile achieved via protonation such that physical and/or chemical degradation reactions are minimized. For a therapeutic peptide, the extent of protonation required for stability, and thus the amount of the ionization stabilizing excipient required in the solution, will depend on, among other things, the primary structure (i.e., amino acid sequence) and the peptide concentration in the solution.

Each molecule that functions as an ionization stabilizing excipient will exhibit a certain tendency to donate protons to the therapeutic molecule(s) in a given solvent system; this tendency to donate protons may be referred to as the relative acidic strength of the molecule. For a fixed concentration of a proton-donating molecule, (and for simplicity it is assumed only monoprotic molecules in this example) molecules that have a greater acidic strength will protonate the therapeutic molecule to a greater extent than a weaker acid. Accordingly, the concentration of a given proton-donating molecule (ionization stabilizing excipient) required to achieve an appropriate or optimal ionization profile for the therapeutic molecules will be inversely proportional to its acidic strength. These and other non-limiting aspects of the present invention are discussed herein.

In certain aspects the aprotic polar solvent can be deoxygenated prior to preparation of the formulation. Many different techniques can be used in the context of the present invention to deoxygenate or remove oxygen from aprotic polar solvents (degasification or deoxygenation). For instance, it is contemplated that deoxygenation can, but is not limited to, remove oxygen that is dissolved in a liquid aprotic polar solvent either by the liquid alone, by the liquid and other solute molecules (e.g. micelles, cyclodextrins, etc.), or by other solute molecules alone. Non-limiting examples of deoxygenation techniques include placing the aprotic polar solvent under reduced pressure and/or heating the liquid to decrease the solubility of dissolved gas, fractional distillation, membrane degasification, substitution by inert gas, using a reducing agent, freeze-pump-thaw cycling, or long time storage in a container with air-locks. In one embodiment, the aprotic polar solvent is deoxygenated by vacuum degasification. In another embodiment the aprotic polar solvent is deoxygenated by using a deaerator. In one instance, the deaerator is a tray-type or cascade type deaerator. In another instance, the deaerator is a spray-type deaerator. In yet another embodiment, the aprotic polar solvent is deoxygenated using a gas-liquid separation membrane. In one instance, the aprotic polar solvent is degassed using a gas-liquid separation membrane and reduced pressure. In one embodiment a non-oxygen gas (e.g., $N_2$) is bubbled through the liquid to replace or reduce oxygen in the aprotic polar solvent. In one instance, the gas bubbled through the aprotic polar solvent is argon, helium, nitrogen, an inert gas, and/or hydrogen gas, preferably nitrogen gas. In another instance the gas is bubbled through the aprotic polar solvent using a gas-stripping column. In yet another embodiment, the aprotic polar solvent is deoxygenated by one or more reducing agent(s). Non-limiting examples of reducing agents include ammonium sulfite, hydrogen gas, active deoxygenating metals, copper, tin, cadmium, Wood's metal alloy (50% bismuth, 25% lead, 12.5% tin, and 12.5% cadmium), etc. In yet another embodiment the aprotic polar solvent is degassed by freeze-pump-thaw cycling (e.g., at least 1, 2, 3, or more cycles can be used). In one instance the freeze-pump-thaw cycle comprises freezing the aprotic polar solvent under liquid nitrogen, applying a vacuum, and then thawing the solvent in warm water. In one embodiment the aprotic polar solvent is deoxygenated by long time storage in a steel, glass, or wood container. In another embodiment, the aprotic polar solvent is sonicated, ultrasonicated, or stirred during deoxygenation.

Once treated or deoxygenated, the aprotic polar solvents may have less than 0.1 mM of dissolved oxygen, preferably less than 0.05 mM of dissolved oxygen. Methods known to those of skill in the art can be used to determine the amount of dissolved oxygen in any given aprotic polar solvent (e.g., a dissolved oxygen meter or probe device can be used such as the Dissolved Oxygen Probe commercially available by Vernier (Beaverton, Oreg., USA)).

In certain aspects the formulations disclosed in the present application can be prepared and/or sealed under an inert gas atmosphere. Common methods include backfilling the primary container-closure system (e.g. vials) to provide an inert gas (e.g. nitrogen, argon) headspace. A secondary container-closure system (e.g. sealed foil pouches) may also be sealed under an inert gas environment.

I. Therapeutic Agents

Therapeutic agents in the context of the present invention encompass peptide or protein compounds, small molecule drugs, and pharmaceutically acceptable salts thereof. When the therapeutic agent is present in the deoxygenated aprotic polar solvent, the stability of the therapeutic agent may be further enhanced when compared with the same therapeutic agent present in an untreated aprotic polar solvent. The increased stability can be attributed due, at least in part, to a reduction in the oxidative degradation of the therapeutic agent or the oxidative degradation of the aprotic polar solvent, or both. One of skill is aware of which therapeutic agent is suitable for treating certain diseases or conditions and would be capable of administering effective amounts of a therapeutic agent in a formulation as described herein for the treatment of a disease or condition.

Non-limiting examples of peptides and proteins (and salts thereof) that can be used in the context of the present invention include, but are not limited to, glucagon, pramlintide, insulin, leuprolide, an luteinizing-hormone-releasing hormone (LHRH) agonist, parathyroid hormone (PTH), amylin, angiotensin(1-7), botulinum toxin, hematide, an amyloid peptide, gastric inhibitory peptide, an insulin-like growth factor, growth hormone releasing factor, anti-microbial factor, glatiramer, glucagon-like peptide-1 (GLP-1), a GLP-1 agonist, exenatide, analogs thereof, an amylin analog (pramlintide), and mixtures thereof. In some preferred aspects, therapeutic agent is glucagon, insulin and/or pramlintide.

Non-limiting examples of small molecule drugs (and salts thereof) that can be used in the context of the present invention include, but are not limited to, epinephrine, benzodiazepines, catecholemines, "triptans," sumatriptan, novantrone, chemotherapy small molecules (e.g., mitoxantrone), corticosteroid small molecules (e.g., methylprednisolone, beclomethasone dipropionate), immunosuppressive small molecules (e.g., azathioprine, cladribine, cyclophosphamide monohydrate, methotrexate), anti-inflammatory small molecules (e.g., salicylic acid, acetylsalicylic acid, lisofylline, diflunisal, choline magnesium trisalicylate, salicylate, benorylate, flufenamic acid, mefenamic acid, meclofenamic acid, triflumic acid, diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin, sulindac, phenylbutazone, oxyphenbutazone, azapropazone, feprazone, piroxicam, isoxicam), small molecules used to treat neurological disorders (e.g., cimetidine, ranitidine, famotidine, nizatidine, tacrine, 21inblasti, metrifonate, rivastigmine, selegilene, imipramine, fluoxetine, olanzapine, sertindole, risperidone, valproate semisodium, gabapentin, carbamazepine, topiramate, phenytoin), small molecules used to treat cancer (e.g., vincristine, 21inblastine, paclitaxel, docetaxel, cisplatin, irinotecan, topotecan, gemcitabine, temozolomide, imatinib, bortezomib), statins (e.g., atorvastatin, amlodipine, rosuvastatin, sitagliptin, simvastatin, fluvastatin, pitavastatin, lovastatin, pravastatin, simvastatin), and other taxane derivatives, small molecules used to treat tuberculosis (e.g., rifampicin), small molecule anti-fungal agents (e.g., fluconazole), small molecule anti-anxiety agents and small molecule anti-convulsant agents (e.g., lorazepam), small molecule anti-cholinergic agents (e.g., atropine), small molecule β-agonist drugs (e.g., albuterol sulfate), small molecule mast cell stabilizers and small molecule agents used to treat allergies (e.g., cromolyn sodium), small molecule anesthetic agents and small molecule anti-arrhythmic agents (e.g., lidocaine), small molecule antibiotic agents (e.g., tobramycin, ciprofloxacin), small molecule anti-migraine agents (e.g., sumatriptan), and small molecule anti-histamine drugs (e.g., diphenhydramine). In preferred embodiments, the small molecule is epinephrine.

The therapeutic agent of the invention can be administered intracutaneously in the prevention, diagnosis, alleviation, treatment, or cure of disease. Examples of proteins and proteinaceous compounds which may be formulated and employed in the delivery system according to the present invention include those proteins which have biological activity or which may be used to treat a disease or other pathological conditions.

Each of the aforementioned peptides, proteins, and small molecule drugs are well-known and commercially available from a variety of manufacturers and sources. Further, the amount of the peptides, proteins, or small molecule drugs in the dosage formulations can be varied depending on current acceptable amounts, subject/patient needs (e.g., age, health, weight, nature and extend of symptom), and the like.

The therapeutic agents provided by the manufacturer or commercial source are typically provided in a powdered form for dissolution in to the formulations as described herein. A number of known techniques can be used to form a powdered agent for dissolution.

Any suitable dosage of peptide or peptides can be formulated in the stable formulations of the present invention. Generally, the peptide (or, in embodiments comprising two or more peptides, each of the peptides) is present in the formulation in an amount ranging from about 0.1 mg/mL to about 100 mg/mL. In some embodiments, the peptide is present in the formulation in an amount ranging from about 5 mg/mL to about 60 mg/mL. In other embodiments, the peptide is present in the formulation in an amount ranging from about 10 mg/mL to about 50 mg/mL. In still other embodiments, the peptide is present in the formulation in an amount ranging from about 1 mg/mL to about 15 mg/mL. In yet other embodiments, the peptide is present in the formulation in an amount ranging from about 0.5 mg/mL to about 5 mg/mL. In yet other embodiments, the peptide is present in the formulation in an amount ranging from about 1 mg/mL to about 50 mg/mL. Again, it will be readily apparent to those of skill that the peptide dosage can be varied depending on the peptide used and the disease, disorder or condition to be treated.

In some embodiments, the formulations of the present invention further comprise an antioxidant. In other embodiments, the formulations further comprise a chelator. In still other embodiments, the formulations of the present invention further comprise a preservative.

II. Formulations

Formulations of the present invention include a therapeutic agent present in an aprotic polar solvent system containing at least one ionization stabilizing excipient. The therapeutic agent can be dissolved (e.g., fully or partially solubilized) or suspended (fully or partially) in the aprotic polar solvent system. Further, the formulation can be structured as a single phase solution, a paste or slurry, a gel, an emulsion, or a suspension.

In some embodiments, the therapeutic agent is present in an aprotic polar solvent that is "neat," i.e., that does not contain a co-solvent. In other embodiments the therapeutic agent is present in a solvent system that is a mixture of two or more aprotic polar solvents (i.e., an aprotic polar solvent system). An example would be a 75/25 (% v/v) mixture of DMSO and NMP. In some embodiments, however, a co-solvent can be used, where in one or more aprotic polar solvents are mixed with a co-solvent. Non-limiting examples of co-solvents include water, ethanol, propylene glycol (PG), glycerol, and mixtures thereof. In certain aspects water can be specifically excluded or limited as a co-solvent, i.e., the co-solvent can be a non-aqueous co-solvent. The co-solvent may be present in the formulation in an amount ranging from about 0.5% (w/v) to about 50% (w/v), e.g., about 1%, about 5%, about 10%, about 15%, about 20%, about 25%, about 30%, about 35%, or about 40% (w/v). In some embodiments, the co-solvent is present in the formulation in an amount ranging from about 10% (w/v) to about 50% (w/v), from about 10% (w/v) to about 40% (w/v), from about 10% (w/v) to about 30% (w/v), from about 10% (w/v) to about 25% (w/v), from about 15% (w/v) to about 50% (w/v), from about 15% (w/v) to about 40% (w/v), from about 15% (w/v) to about 30% (w/v), or from about 15% (w/v) to about 25% (w/v).

Still further, the formulations of the present invention can include one or more other excipients in addition to the ionization stabilizing excipient. In some embodiments, the other excipient is selected from sugars, starches, sugar alcohols, antioxidants, chelators, and preservatives. Examples of suitable sugars excipients include, but are not limited to trehalose, glucose, sucrose, etc. Examples of suitable starches for stabilizing excipients include, but are not limited to, hydroxyethyl starch (HES). Examples of suitable sugar alcohols (also referred to as polyols) for stabilizing excipients include, but are not limited to, mannitol and sorbitol. Examples of suitable antioxidants include, but are not limited to, ascorbic acid, cysteine, methionine, monothioglycerol, sodium thiosulphate, sulfites, BHT, BHA, ascorbyl palmitate, propyl gallate, N-acetyl-L-cysteine (NAC), and Vitamin E. Examples of suitable chelators include, but are not limited to, EDTA, EDTA disodium salt (edetate disodium), tartaric acid and salts thereof, glycerin, and citric acid and salts thereof. Examples of suitable inorganic salts include sodium chloride, potassium chloride, calcium chloride, magnesium chloride, calcium sulfate, and magnesium sulfate. Examples of suitable preservatives include, but are not limited to, benzyl alcohols, methyl parabens, propyl parabens, and mixtures thereof. Additional formulation components include local anesthetics, such lidocaine or procaine. In some embodiments, the additional stabilizing excipient is present in the formulation in an amount ranging from about 0.05% (w/v) to about 60% (w/v), from about 1% (w/v) to about 50% (w/v), from about 1% (w/v) to about 40% (w/v), from about 1% (w/v) to about 30% (w/v), from about 1% (w/v) to about 20% (w/v), from about 5% (w/v) to about 60% (w/v), from about 5% (w/v) to about 50% (w/v), from about 5% (w/v) to about 40% (w/v), from about 5% (w/v) to about 30% (w/v), from about 5% (w/v) to about 20% (w/v), from about 10% (w/v) to about 60% (w/v), from about 10% (w/v) to about 50% (w/v), from about 10% (w/v) to about 40% (w/v), from about 10% (w/v)

to about 30% (w/v), or from about 10% (w/v) to about 20% (w/v). In some embodiments, the additional stabilizing excipient is present in the formulation in an amount that is about, at most, or at least 0.1, 0.5, 1, 2, 3, 4, 5, 6, 7, 8, 9, 10, 15, 20, 25, 30, 35, 40, 45, 50, 55, or 60% (w/v).

III. Therapeutic Methods

In another aspect, the present invention provides methods of treating diseases, conditions, or disorders by administering to a subject a therapeutic agent for treating a disease, condition, or disorder in a stable formulation as described herein in an amount effective to treat, alleviate, or prevent the disease, condition, or disorder.

In some embodiments, a therapeutic method of the present invention comprises treating hypoglycemia by administering to a subject having hypoglycemia a therapeutic agent for hypoglycemia in a stable formulation as described herein in an amount effective to treat the hypoglycemia. In some embodiments, the subject is administered a stable formulation comprising glucagon. In certain aspects hypoglycemia can be caused by diabetes or non-diabetes related diseases, conditions, and disorders.

As described by the Workgroup of the American Diabetes Association and the Endocrine Society, (Seaquist, et al, (2013), *Diabetes Care*, Vol 36, pages 1384-1395) with respect to hypoglycemia a single threshold value for plasma glucose concentration that defines hypoglycemia in diabetes is not typically assigned because glycemic thresholds for symptoms of hypoglycemia (among other responses) shift to lower plasma glucose concentrations after recent antecedent hypoglycemia and to higher plasma glucose concentrations in patients with poorly controlled diabetes and infrequent hypoglycemia.

Nonetheless, an alert value can be defined that draws the attention of both patients and caregivers to the potential harm associated with hypoglycemia. Patients at risk for hypoglycemia (i.e., those treated with a sulfonylurea, glinide, or insulin) should be alert to the possibility of developing hypoglycemia at a self-monitored plasma glucose—or continuous glucose monitoring subcutaneous glucose—concentration of ≤70 mg/dL (≤3.9 mmol/L). Because it is higher than the glycemic threshold for symptoms in both nondiabetic individuals and those with well-controlled diabetes, it generally allows time to prevent a clinical hypoglycemic episode and provides some margin for the limited accuracy of monitoring device at low-glucose levels.

The condition of severe hypoglycemia is an event requiring assistance of another person to actively administer carbohydrates, glucagon, or take other corrective actions. Plasma glucose concentrations may not be available during an event, but neurological recovery following the return of plasma glucose to normal is considered sufficient evidence that the event was induced by a low plasma glucose concentration. Typically, these events begin occurring at plasma glucose concentrations of ≤50 mg/dL (2.8 mmol/L). Documented symptomatic hypoglycemia is an event during which typical symptoms of hypoglycemia are accompanied by a measured plasma glucose concentration ≤70 mg/dL (≤3.9 mmol/L). Asymptomatic hypoglycemia is an event not accompanied by typical symptoms of hypoglycemia but with a measured plasma glucose concentration ≤70 mg/dL (≤3.9 mmol/L). Probable symptomatic hypoglycemia is an event during which symptoms typical of hypoglycemia are not accompanied by a plasma glucose determination but that was presumably caused by a plasma glucose concentration ≤70 mg/dL (≤3.9 mmol/L). Pseudo-hypoglycemia is an event during which the person with diabetes reports any of the typical symptoms of hypoglycemia with a measured plasma glucose concentration >70 mg/dL (>3.9 mmol/L) but approaching that level.

Further included in the indications which may be treated by the disclosed invention are hypoglycemia-associated autonomic failure (HAAF). As described by Philip E. Cryer, Perspectives in Diabetes, Mechanisms of Hypoglycemia-Associated Autonomic Failure and Its Component Syndromes in Diabetes, Diabetes, Vol. 54, pp. 3592-3601 (2005), "recent antecedent iatrogenic hypoglycemia causes both defective glucose counter-regulation (by reducing epinephrine responses to a given level of subsequent hypoglycemia in the setting of absent decrements in insulin and absent increments in glucagon) and hypoglycemia unawareness (by reducing sympathoadrenal and the resulting neurogenic symptom responses to a given level of subsequent hypoglycemia) and thus a vicious cycle of hypoglycemia." HAAF affects those with type 1 and advanced type 2 diabetes. Additionally, the invention of the present disclosure may also treat hypoglycemia in patients following islet cell transplantation.

The formulations of the present invention can also be used for the treatment of hyperinsulinemic hypoglycemia, which broadly refers to the condition and effects of low blood glucose levels that are caused by excessive insulin. The most common type of severe, but typically transient, hyperinsulinemic hypoglycemia arises from the administration of exogenous insulin in patients with Type 1 diabetes. This type of hypoglycemia can be defined as iatrogenic hypoglycemia, and is a limiting factor in the glycemic management of type 1 and type 2 diabetes. Nocturnal hypoglycemia (night-time hypo) is a common type of iatrogenic hypoglycemia arising in patients taking exogenous insulin. However, hyperinsulinemic hypoglycemia can also arise due to endogenous insulin, for example in congenital hyperinsulinism, insulinomas (insulin-secreting tumors), exercise-induced hypoglycemia and reactive hypoglycemia. Reactive hypoglycemia is a non-diabetic hypoglycemia, and is due to low blood sugar that occurs following a meal—typically within four hours after eating. Reactive hypoglycemia may also be referred to as postprandial hypoglycemia. Symptoms and signs of reactive hypoglycemia can include hunger, weakness, shakiness, sleepiness, sweating, confusion and anxiety. Stomach surgery (e.g. bariatric surgery) is one possible cause, as following surgery food may pass too quickly into the small intestine. Additional causes include enzyme deficiencies that make it difficult for the body to breakdown food, or increased sensitivity to the hormone ephinephrine.

In some embodiments, the disease, condition, or disorder to be treated with a stable formulation of the present invention is a diabetic condition. Examples of diabetic conditions include, but are not limited to, type 1 diabetes, type 2 diabetes, gestational diabetes, pre-diabetes, hyperglycemia, hypoglycemia, and metabolic syndrome. In some embodiments, the disease, condition, or disorder is hypoglycemia. In some embodiments, the disease, condition, or disorder is diabetes.

In some embodiments, a therapeutic method of the present invention comprises treating diabetes by administering to a subject having diabetes a therapeutic agent in a stable formulation as described herein in an amount effective to treat the diabetes. In some embodiments, the subject is administered a stable formulation comprising insulin. In some embodiments, the subject is administered a stable formulation comprising pramlintide. In some embodiments, the subject is administered a stable formulation comprising insulin and pramlintide. In some embodiments, the subject is administered a stable formulation comprising exenatide. In some embodiments, the subject is administered a stable formulation comprising glucagon and exenatide.

In certain aspects epinephrine can be administered to a subject at risk of or suspected of anaphylaxis. Epinephrine is indicated as an emergency treatment of Type I allergic reactions which can arise from multiple sources, including, but not limited to, foods, drugs and/or other allergens, allergen immunotherapy, diagnostic testing substances, insect stings and bites, and idiopathic or exercise-induced anaphylaxis.

Administered dosages for the peptide or small molecule drugs as described herein for treating a disease, condition, or disorder (e.g., a diabetic condition, hypoglycemia, or anaphylaxis) are in accordance with dosages and scheduling regimens practiced by those of skill in the art. General guidance for appropriate dosages of all pharmacological agents used in the present methods is provided in Goodman and Gilman's The Pharmacological Basis of Therapeutics, 11th Edition, 2006, supra, and in a Physicians' Desk Reference (PDR), for example, in the 65th (2011) or 66th (2012) Eds., PDR Network, LLC, each of which is hereby incorporated herein by reference. The appropriate dosage of a peptide drug for treating a disease, condition, or disorder as described herein will vary according to several factors, including the formulation of the composition, patient response, the severity of the condition, the subject's weight, and the judgment of the prescribing physician. Effective doses of the described formulations deliver a medically effective amount of a peptide drug. The dosage can be increased or decreased over time, as required by an individual patient or determined by medical personnel.

Determination of an effective amount or dose is well within the capability of those skilled in the art, especially in light of the detailed disclosure provided herein. Generally, the formulations to deliver these doses may contain one, two, three, four, or more small molecules, peptides, or peptide analogs (collectively "peptide," unless peptide analogs are expressly excluded), wherein each peptide is present at a concentration from about 0.1 mg/mL up to the solubility limit of the peptide in the formulation. This concentration is preferably from about 1 mg/mL to about 100 mg/mL. In certain aspects the concentration is about 1 mg/mL, about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, or about 100 mg/mL. The concentrations for small molecules are known to medical personnel and can be established and implemented using the disclosure provided herein, e.g., 0.01 mg/ml to 500 mg/ml, or in doses of 5, 10, 25, 50, 75, 100, 200, 500, to 1000 mg including all values and ranges there between.

The formulations of the present invention may be for subcutaneous, intradermal, or intramuscular administration (e.g., by injection or by infusion). In some embodiments, the formulation is administered subcutaneously. The formulations can also be delivered transdermally, such as by topically applying the composition to skin (e.g., spreading the composition on skin or loading the composition onto a dermal patch and attaching the dermal patch to the skin).

The formulations of the present disclosure can be administered by infusion or by injection using any suitable device. For example, a formulation of the present invention may be placed into a syringe (e.g., a pre-filled syringe), a pen injection device, an auto-injector device, or a pump device. In some embodiments, the injection device is a multi-dose injector pump device or a multi-dose auto-injector device. The formulation is presented in the device in such a fashion that the formulation is readily able to flow out of the needle upon actuation of an injection device, such as an auto-injector, in order to deliver the peptide drugs. Suitable pen/auto injector devices include, but are not limited to, those pen/auto injection devices manufactured by Becton-Dickenson, Swedish Healthcare Limited (SHL Group), YpsoMed Ag, and the like. Suitable pump devices include, but are not limited to, those pump devices manufactured by Tandem Diabetes Care, Inc., Delsys Pharmaceuticals and the like.

In some embodiments, the formulations of the present invention are provided ready for administration in a vial, a cartridge, or a pre-filled syringe.

In some embodiments, the stable formulation is used for formulating a medicament for the treatment of hypoglycemia. In some embodiments, the stable formulation comprises glucagon or a salt thereof (e.g., glucagon acetate). In some embodiments, the stable formulation comprises glucagon and exenatide.

In some embodiments, the stable formulation is used for formulating a medicament for the treatment of diabetes. In some embodiments, the stable formulation comprises insulin. In some embodiments, the stable formulation comprises exenatide. In some embodiments, the stable formulation comprises pramlintide. In some embodiments, the stable formulation comprises insulin and pramlintide.

IV. Kits/Containers

Kits are also contemplated as being used in certain aspects of the present invention. For instance, a formulation of the present invention can be included within a kit. A kit can include a container. In one aspect, for instance, the formulation can be comprised within a container that is ready to administer to a subject without having to reconstitute or dilute the formulation. That is, the formulation to be administered can be stored in the container and be readily used as needed. The container can be a device. The device can be a syringe (e.g. pre-filled syringe), a pen injection device, an auto-injector device, a device that can pump or administer the formulation (e.g., automatic or non-automatic external pumps, implantable pumps, etc.) or a perfusion bag. Suitable pen/auto-injector devices include, but are not limited to, those pen/auto-injection devices manufactured by Becton-Dickenson, Swedish Healthcare Limited (SHL Group), YpsoMed Ag, and the like. Suitable pump devices include, but are not limited to, those pump devices manufactured by Tandem Diabetes Care, Inc., Delsys Pharmaceuticals and the like.

V. Examples

A number of peptide and small molecule formulations were prepared using the methods disclosed in the present application and also via the methods disclosed in the prior art (e.g. direct dissolution of a peptide in an aprotic polar solvent system, and drying down the peptide from a buffered aqueous solution prior to dissolution in an aprotic polar solvent system). As will be shown in the examples below, the compositions prepared by the methods of the present invention provided physical and chemical stability that exceeded that observed via direct dissolution of the peptide powder in the aprotic polar solvent system.

Some embodiments of the present disclosure will be described in greater detail by way of specific examples. The following examples are offered for illustrative purposes, and are not intended to limit any present invention in any manner. For example, those of skill in the art will readily recognize a variety of noncritical parameters which can be changed or modified to yield essentially the same results.

Example 1

In this example, glucagon solutions were prepared by dissolving glycine hydrochloride (CAS No. 6000-43-7) directly in DMSO (CAS No. 67-68-5) at 5 mM, 10 mM, and 20 mM concentrations, followed by dissolution of glucagon powder (MW=3483 g/mol; purchased from Bachem AG) to a peptide concentration of 5 mg/mL. The prepared sample solutions are shown in Table 1:

TABLE 1

Glucagon sample solutions prepared by dissolving both glycine hydrochloride and glucagon powder directly in DMSO.

| Glucagon Concentration | Solvent | Added Excipient |
| --- | --- | --- |
| 5 mg/mL | DMSO | 5 mM Glycine Hydrochloride |
| 5 mg/mL | DMSO | 10 mM Glycine Hydrochloride |
| 5 mg/mL | DMSO | 20 mM Glycine Hydrochloride |

The reversed-phase high performance liquid chromatography (RP-HPLC) method used to assess chemical stability was a gradient method with mobile phases A and B respectively consisting of 0.1% (v/v) TFA (trifluoroacetic acid) in water and 0.1% (v/v) TFA in acetonitrile. A C8 column (BioBasic™-8; ThermoScientific) (4.6 mm I.D.×250 mm length, 5 micron particle size) was used with a column temperature of 37° C., a 1.0 mL/min flow rate, 6-µL sample injection volume and 280-nm detection wavelength.

Visual observation indicated that following six weeks (42 days) of storage at 40° C., the sample solutions containing glycine hydrochloride as a formulation excipient remained clear and colorless, and did not exhibit any precipitation and/or gelation. The stability of 5 mg/mL glucagon formulations were assessed via RP-HPLC as described above.

The sample formulations prepared with varying concentrations of glycine hydrochloride were sealed in 2-mL CZ vials (Crystal-Zenith, West Pharmaceuticals, PA, USA) with 13-mm FluroTec® stoppers (rubber stoppers coated with a fluorocarbon film, produced by West Pharmaceuticals) and stored at 40° C. for up to 6 weeks. The solutions were compared with 5 mg/mL glucagon formulations prepared via drying from a non-volatile buffer and reconstituting in DMSO (the pH memory formulations as described in Prestrelski '644), and direct dissolution of glucagon in DMSO (the method as described in Stevenson '547). The stability of the formulations are presented as glucagon purity and shown in Table 2 below.

TABLE 2

Stability (provided as peptide purity) of 5 mg/mL glucagon solutions stored at 40° C.

| Time Point | Glycine HCl Concentration | | | pH Memory Formulation | Direct Dissolution In DMSO |
| --- | --- | --- | --- | --- | --- |
| | 5 mM | 10 mM | 20 mM | | |
| Day 1 | 100% | 100% | 100% | 100% | Formed Gel |
| Day 14 | 99.7% | 99.5% | 99.3% | 99.4% | — |
| Day 42 | 97.8% | 97.0% | 97.0% | 96.8% | — |

Within 24 hours at room temperature, the 5 mg/mL glucagon solutions (approximately 0.45% w/w) prepared by direct dissolution of glucagon powder in DMSO exhibited physical aggregation, as noted by the formation of insoluble material (FIG. 1). By contrast, solutions prepared with 5 mg/mL glucagon powder dissolved in DMSO in the presence of 5.0 mM glycine HCl remained clear (i.e. free of precipitation) and colorless throughout the examined incubation period (6 weeks at 40° C.). Glucagon formulations that had previously been lyophilized from a buffered aqueous solution containing 1 mg/mL glucagon, 2 mM glycine and 1% (w/v) trehalose prior to reconstitution to 5-fold the initial concentration with DMSO (i.e., the composition in the aprotic polar solvent system following reconstitution was 5 mg/mL glucagon, 10 mM glycine, and 5% (w/v) trehalose) also exhibited a glucagon purity of approximately 97% following six weeks of storage at 40° C.

Accordingly, the compositions prepared by the method of the present invention provide enhanced stability compared to the prior art methods of direct dissolution of the peptide powder in an aprotic polar solvent. Further, the formulations of the present invention may provide an alternative pathway for preparing highly-concentrated, stable glucagon formulations in aprotic polar solvent systems without the need for drying the peptide from a buffered aqueous solution prior to dissolution in the aprotic polar solvent system.

Example 2

In this example glucagon solutions were prepared at a concentration of 5 mg/mL by dissolving glucagon powder in DMSO that included different concentrations of added hydrochloric acid, ranging from 0.001 M (1 mM) to 0.01 M (10 mM). To minimize the amount of water added to the formulation, 5 N HCl was utilized to prepare 10 mM and 5.6 mM HCl in DMSO solutions, while 1 N HCl was used to prepare the 3.2 mM, 1.8 mM, and 1.0 mM solutions. As an example, the 10 mM HCl in DMSO solution was prepared by adding 20 µL of 5 N HCl to 9.98 mL of DMSO (neat), while the 1.0 mM HCl in DMSO solution was prepared by adding 10 µL of 1 N HCl to 9.99 mL of DMSO (neat). Samples of each formulation were stored in CZ vials and incubated at 40° C.

Following both 28 and 58 days of storage the chemical stability of the peptide was assessed by RP-HPLC and the purity reported in Table 3. The addition of 1.0 mM HCl was insufficient to prevent the formation of insoluble aggregates in the 5 mg/mL glucagon solutions, and accordingly the chemical stability of these samples were not measured. Conversely, the glucagon molecule exhibited relatively rapid chemical degradation when 10 mM HCl was added to the solution. Decreasing the added HCl concentration in the solution increased the overall stability of the glucagon molecule, with the 3.2 mM and 1.8 mM HCl solutions exhibiting the highest stability over the examined time period.

TABLE 3

Stability (provided as peptide purity) of 5 mg/mL Glucagon-DMSO Solutions Stored at 40° C.

| Glucagon | Added [HCl] | Day 28 | Day 58 |
| --- | --- | --- | --- |
| 5 mg/mL | 10.0 mM | 36.9% | 0% |
| 5 mg/mL | 5.6 mM | 90.8% | 85.3% |
| 5 mg/mL | 3.2 mM | 98.0% | 96.8% |
| 5 mg/mL | 1.8 mM | 98.3% | 97.4% |
| 5 mg/mL | 1.0 mM | Insoluble Aggregates | Insoluble Aggregates |

Example 3

Sample solutions were prepared by dissolving glucagon powder to a concentration of 5 mg/mL in DMSO which contained various added concentrations of glycine hydrochloride (CAS No. 6000-43-7), betaine hydrochloride (CAS No. 590-46-5), or hydrochloric acid (1 N; CAS No. 7647-01-0). The various concentrations of each ionization stabilizing excipient used to prepare the sample formulations are listed in Table 4. Samples of each formulation were stored in CZ vials and incubated at 40° C. Following 28 days of storage the chemical stability of the glucagon peptide was assessed by RP-HPLC and the purity reported in Table 4. This example demonstrates that the proton-donating ability of the added ionization stabilizing excipient (i.e. its 'strength') may influence the concentration required to stabilize the therapeutic molecule. Glucagon was selected as a model peptide due to its tendency to gel (i.e. form insoluble aggregates) when the molecule is insufficiently protonated. A concentration of up to 2 mM glycine hydrochloride was insufficient to prevent the formation of insoluble aggregates in the solution, though this concentration of both betaine hydrochloride and hydrochloric acid was sufficient to prevent the formation of insoluble aggregates following 28 days of storage at 40° C.

TABLE 4

Stability (provided as % peptide purity) of 5 mg/mL Glucagon-DMSO Solutions Stored at 40° C. for 28 days.

| Glucagon Powder | Ionization Stabilizing Excipient | Added Concentration | % Peptide Purity |
| --- | --- | --- | --- |
| 5 mg/mL | Glycine HCl | 0.5 mM | Insoluble Aggregates |
| 5 mg/mL | Glycine HCl | 1.0 mM | Insoluble Aggregates |
| 5 mg/mL | Glycine HCl | 2.0 mM | Insoluble Aggregates |
| 5 mg/mL | Glycine HCl | 3.0 mM | 98.5% |
| 5 mg/mL | Glycine HCl | 4.0 mM | 98.6% |
| 5 mg/mL | Glycine HCl | 5.0 mM | 99.1% |
| 5 mg/mL | Betaine HCl | 0.5 mM | Insoluble Aggregates |
| 5 mg/mL | Betaine HCl | 2.0 mM | 98.6% |
| 5 mg/mL | Betaine HCl | 5.0 mM | 98.4% |
| 5 mg/mL | HCl | 1.0 mM | Insoluble Aggregates |
| 5 mg/mL | HCl | 1.8 mM | 98.3% |
| 5 mg/mL | HCl | 3.2 mM | 98.0% |

Example 4

The following example demonstrates the stability of a glucagon solution prepared according to the method of the present invention in the presence of added formulation components (e.g. inactive agents, excipients). Sample solutions were prepared by dissolving glucagon powder to a concentration of 5 mg/mL in DMSO which contained about 3.2 mM of added HCl (from a stock solution of 1 N HCl). To these solutions were added varying concentrations of moisture, as well as 5.5% (w/v) mannitol (CAS No. 69-65-8), and 1% (v/v) benzyl alcohol (CAS No. 100-51-6). The experimental samples examined are listed in Table 5.

Samples of each formulation were stored in CZ vials and incubated at room temperature (22-23° C.). Following 180 days (6 months) of storage the chemical stability of the glucagon peptide was assessed by RP-HPLC (according to the method described in Example 1) and the glucagon purity is reported in Table 5. This example demonstrates that additional formulation components (e.g. inactive agents, excipients) may be included in the formulation and still yield a stable formulation following approximately 6 months of storage at room temperature.

TABLE 5

Stability of 5 mg/mL Glucagon-DMSO Solutions stored at room temperature for 180 days. Stability is provided as % glucagon purity as assessed by RP-HPLC

| Glucagon | Added [HCl] | Moisture (% v/v) | Mannitol (% w/v) | Benzyl Alcohol (% v/v) | % Glucagon Purity |
| --- | --- | --- | --- | --- | --- |
| 5 mg/mL | 3.2 mM | 0% | 0% | 0% | 98.2 |
| 5 mg/mL | 3.2 mM | 1% | 0% | 0% | 98.3 |
| 5 mg/mL | 3.2 mM | 3% | 0% | 0% | 98.1 |
| 5 mg/mL | 3.2 mM | 5% | 0% | 0% | 98.4 |
| 5 mg/mL | 3.2 mM | 1% | 5.5% | 0% | 98.6 |
| 5 mg/mL | 3.2 mM | 3% | 5.5% | 0% | 97.7 |
| 5 mg/mL | 3.2 mM | 5% | 5.5% | 0% | 98.9 |
| 5 mg/mL | 3.2 mM | 1% | 5.5% | 1% | 95.3 |
| 5 mg/mL | 3.2 mM | 3% | 5.5% | 1% | 96.9 |
| 5 mg/mL | 3.2 mM | 5% | 5.5% | 1% | 97.1 |

Example 5

Formulations of the amylin analogue, pramlintide, were prepared at a concentration of 1 mg/mL by dissolving pramlintide acetate powder (molecular weight=3949.4; CAS No. 196078-30-5; ChemPep, Inc., Wellington, Fla.) in DMSO in the presence of 5 mM glycine hydrochloride (CAS No. 6000-43-7) or 5 mM citric acid, anhydrous (CAS No. 77-92-9). For comparison, pramlintide acetate powder was also dissolved directly in DMSO at the same concentration (but with no added excipients). Samples of each formulation were stored in CZ vials and incubated at 40° C. The sample solutions remained clear (i.e., free of insoluble aggregates) and colorless throughout the studied period. Following 14 and 28 days of storage, the chemical stability of the peptide was assessed by RP-HPLC according the method described in Example 1. As shown in Table 6, the inclusion of both 5 mM glycine HCl and 5 mM citric acid provided enhanced stability compared to solutions containing only pramlintide and DMSO.

TABLE 6

Stability of Pramlintide-DMSO solutions stored at 40° C. (provided as % peptide purity).

| Pramlintide Powder Conc. | Excipient | Day 0 | Day 14 | Day 28 |
|---|---|---|---|---|
| 1 mg/mL | None | 100% | 77.5% | 49.1% |
| 1 mg/mL | 5 mM Glycine HCl | 100% | 100% | 100% |
| 1 mg/mL | 5 mM Citric Acid | 100% | 91.1% | 76.6% |

Example 6

Formulations of the amylin analog, pramlintide, were prepared by dissolving pramlintide acetate powder in DMSO to a concentration of 1 mg/mL, and to which was added different concentrations of hydrochloric acid ranging from 0.00001 M (0.01 mM) to 0.1 M (100 mM). To minimize the amount of water added to the formulation, 5 N HCl was used to prepare the 100 mM and 10 mM HCl in DMSO solutions, while 1 N HCl was used to prepare the 1 mM, 0.1 mM, and 0.01 mM HCl in DMSO solutions. As an example, for the 100 mM HCl in DMSO solution, 10 µL of 1 N HCl was added to 9.99 mL of DMSO. Samples of each formulation were stored in CZ vials and incubated at 40° C. Following 31 days of storage, the chemical stability of the peptide was assessed by RP-HPLC according to the method described in Example 1. The sample solutions remained clear (i.e. free of insoluble material) and colorless throughout the studied period. However, as shown in Table 7, the addition of a specific amount of HCl (1 mM HCl in DMSO) provided enhanced peptide stability, minimizing chemical degradation compared to the other sample formulations.

TABLE 7

Stability (provided as % peptide purity) of 1 mg/mL Pramlintide-DMSO Solutions Stored at 40° C.

| Pramlintide | Added [HCl] mM | Day 0 | Day 31 |
|---|---|---|---|
| 1 mg/mL | 100 | 100% | 0% |
| 1 mg/mL | 10 | 100% | 72.9% |
| 1 mg/mL | 1 | 100% | 100.0% |
| 1 mg/mL | 0.1 | 100% | 72.8% |
| 1 mg/mL | 0.01 | 100% | 43.2% |

Example 7

To further examine the range of added HCl that is capable of stabilizing solutions of pramlintide in DMSO, formulations of the amylin analog, pramlintide, were prepared at a concentration of 1 mg/mL by dissolving pramlintide acetate powder in DMSO in the presence of different concentrations of hydrochloric acid added to the DMSO solution, ranging from 0.00032 (0.32 mM) to 0.00316 M (3.16 mM). The studied HCl concentrations are shown in Table 8. 0.5 mL volumes of the solutions were stored in CZ vials and placed in an incubator with the temperature set to 40° C. The sample formulations remained clear (i.e. free of insoluble material) and colorless throughout the studied period. The stability of the peptide in the formulation (assessed by RP-HPLC according to the method described in Example 1) following 42 days of storage is shown below in Table 8.

TABLE 8

Stability (provided as % peptide purity) of 1 mg/mL Pramlintide-DMSO Solutions Stored at 40° C. for 42 days.

| Pramlintide Powder Concentration | Added [HCl] mM | Peptide Purity |
|---|---|---|
| 1 mg/mL | 3.16 | 69.0% |
| 1 mg/mL | 1.78 | 87.3% |
| 1 mg/mL | 1.26 | 94.9% |
| 1 mg/mL | 1.00 | 97.7% |
| 1 mg/mL | 0.79 | 97.0% |
| 1 mg/mL | 0.56 | 90.5% |
| 1 mg/mL | 0.32 | 59.2% |

Figure 2:
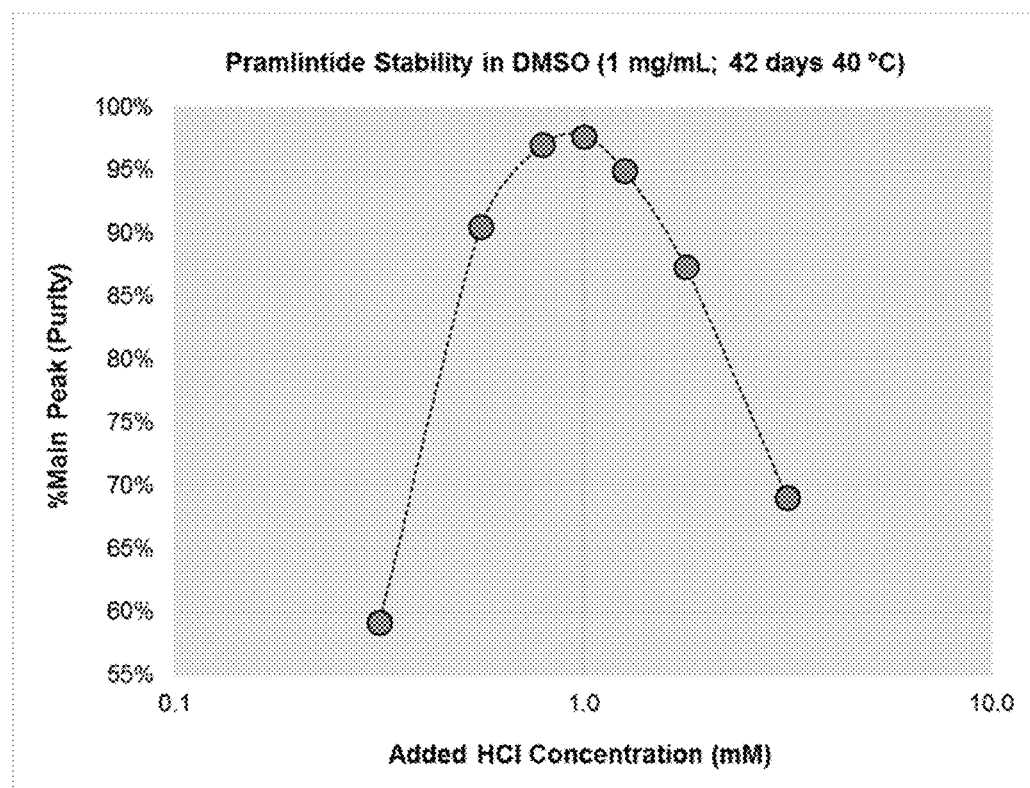
FIG. 2 shows the effect of HCl concentration on pramlintide (1 mg/ml) stability when dissolved in DMSO.

Plotting the data in Table 8 indicates that there may be an optimal range of added ionization stabilizing excipient where peptide stability is optimized (approximately 1.00 mM in this example)(FIG. 2). As noted in FIG. 2 (where the X-axis represents the added HCl concentration (mM) with a logarithmic scale), deviating away from the optimal concentration of added HCl (either by increasing or decreasing the HCl concentration) promotes chemical and/or physical degradation in the solubilized pramlintide molecule.

Example 8

The concentration of an ionization stabilizing excipient required to stabilize a given peptide will depend upon both the amino acid sequence of the peptide and the concentration of the peptide in the solution. In the present example, solutions of pramlintide acetate in DMSO were prepared at two different concentrations: 1 mg/mL and 5 mg/mL. The ionization stabilizing excipient added to the solution was aqueous HCl (5 N and 1 N concentrations), to obtain the final added HCl concentration specified in the left column. The samples were then stored for 1 month (28 days) at 40° C. As noted in Table 9, the stability of the pramlintide molecule as assessed by RP-HPLC according to the method described in Example 1 indicates that increasing the drug concentration five-fold requires an approximately corresponding increase in the concentration of the added HCl required to stabilize the molecule, as the 1 mg/mL pramlintide solutions exhibited maximal stability at 1.00 mM HCl (or between 0.56 mM and 1.78 mM HCl), while the 5 mg/mL solution exhibited maximal stability around 3.16 mM and 5.62 mM HCl).

TABLE 9

Pramlintide stability (provided as % peptide purity) as assessed by RP-HPLC following 28 days storage at 40° C.

| Added HCl Concentration | Pramlintide (1 mg/mL) | Pramlintide (5 mg/mL) |
|---|---|---|
| 10.00 mM | — | 83.5% |
| 5.62 mM | — | 99.3% |
| 3.16 mM | 79.2% | 100.0% |
| 1.78 mM | 96.3% | 88.5% |
| 1.00 mM | 100.0% | 68.9% |
| 0.56 mM | 96.0% | 57.7% |
| 0.32 mM | 67.3% | 56.8% |

* For the 1 mg/mL pramlintide concentration solutions, samples were not prepared at 5.62 mM and 10.0 mM HCl concentration as the formulation exhibited decreasing stability as HCl concentration increased from 1.78 mM to 3.16 mM.

Example 9

In this example, insulin (recombinant human) powder (CAS No. 11061-68-0) was dissolved to a concentration of 3.5 mg/mL in DMSO. Following dissolution of the insulin powder, different concentrations of hydrochloric acid were added to the sample solutions. The concentration of the added HCl ranged from 0.010 M (10 mM) to 0.00032 M (0.32 mM). The studied HCl concentrations are shown in Table 10. 0.5 mL aliquots of the sample insulin solutions were stored in 2-mL CZ vials and placed in an incubator with the temperature set to 40° C. Visual observation of the solutions following storage revealed that they remained clear (i.e. free of insoluble material) and colorless throughout the incubation period. The chemical stability of the peptide in the formulation was assessed by RP-HPLC according to the method described in Example 1 following 14 days of storage and the results (provided as peptide purity) are shown below in Table 10.

TABLE 10

Stability (provided as % peptide purity) of 3.5 mg/mL Insulin-DMSO Solutions Stored at 40° C. for 2 weeks.

| Insulin Powder Concentration | [HCl] mM | Insulin Purity |
| --- | --- | --- |
| 3.5 mg/mL | 10.0 | 70.7% |
| 3.5 mg/mL | 5.6 | 72.4% |
| 3.5 mg/mL | 3.2 | 74.7% |
| 3.5 mg/mL | 1.8 | 88.1% |
| 3.5 mg/mL | 1.0 | 95.5% |
| 3.5 mg/mL | 0.6 | 97.3% |
| 3.5 mg/mL | 0.3 | 94.7% |

Example 10

The following example demonstrates the applicability of the present invention to the preparation of co-formulations. Insulin (recombinant human) powder (CAS No. 11061-68-0) was dissolved to a final concentration of 3.5 mg/mL in DMSO (neat) to which different concentrations of hydrochloric acid had been added. The added concentration of HCl ranged from 0.010 M (10 mM) to 0.00032 M (0.32 mM) as shown in Table 11. Pramlintide acetate powder (CAS No. 196078-30-5) was then added to these solutions to a concentration of 1.0 mg/mL. Accordingly, each of the sample solutions then contained 3.5 mg/mL of insulin powder and 1.0 mg/mL pramlintide powder dissolved in DMSO which contained a specified concentration of added HCl. 0.5 mL aliquots of the sample co-formulation solutions were stored in 2-mL CZ vials, and placed at room temperature (22-23° C.). The stability of the peptide in the formulation was assessed by RP-HPLC (according to the method described in Example 1) following 52 days of storage and the results are shown in Table 11. As with the previous examples directed toward formulations containing a single API, the co-formulations also exhibit an added [HCl] concentration that provides optimal stability to both peptides. The overall purity of the co-formulation is expressed as the sum of the respective insulin and pramlintide purities in the solution.

TABLE 11

Stability of co-formulations (provided as peptide purity) containing 3.5 mg/mL insulin powder and 1.0 mg/mL pramlintide powder dissolved in DMSO and stored at room temperature (22-23° C.) for 52 days.

| Insulin Powder Concentration | Pramlintide Powder Concentration | Added [HCl] | Combined Purity |
| --- | --- | --- | --- |
| 3.5 mg/mL | 1.0 mg/mL | 3.2 mM | 87.4% |
| 3.5 mg/mL | 1.0 mg/mL | 1.8 mM | 92.9% |
| 3.5 mg/mL | 1.0 mg/mL | 1.0 mM | 98.1% |
| 3.5 mg/mL | 1.0 mg/mL | 0.6 mM | 88.8% |
| 3.5 mg/mL | 1.0 mg/mL | 0.3 mM | 87.5% |

Example 11

The following example demonstrates the applicability of the present invention to the preparation of stable formulations of small molecules. Epinephrine (from bitartrate) powder (CAS No. 51-42-3) was dissolved to an API concentration of 10 mg/mL (approximately 55 mM) in DMSO (neat) to which different concentrations of hydrochloric acid (from a 1 N stock solution) had been added. The added concentration of HCl ranged from 1 mM to 100 mM, as shown in Table 12. 0.5 mL aliquots of the epinephrine solutions were stored in 2-mL glass vials and placed in a stability chamber with the temperature set to 40° C. and a relative humidity of 75%. These samples were prepared in an ambient environment and sealed in the vials under an ambient atmosphere.

The stability of the small molecule in the formulation was assessed by RP-HPLC following 1 month of storage and the results are shown in Table 12. For the HPLC analysis, a 1 liter aqueous solution was prepared consisting of 0.05 M monobasic sodium phosphate, 519 mg sodium 1-octanesulfonate, 45 mg edetate disodium, with pH adjusted to 3.8 using $H_3PO_4$. The mobile phase consisted of an 85:15 (v/v) mixture of the aqueous solution with methanol. A BDS Hypersil C8 column (4.6 mm I.D.×150 mm length) was used with a 20-μL injection volume and a 280-nm detection wavelength. Prior to use, the mobile phase was filtered under vacuum through a 0.45-μm nylon filter and the 10 mg/mL epinephrine sample solutions were diluted 200× with mobile phase (e.g. 5 μL sample volume in 1 mL total volume). As epinephrine solutions are susceptible to degradation-promoted discoloration due, in part, to the conversion of the epinephrine molecule via oxidation to adrenochrome (characterized by a pink discoloration of the solution) and/or melanin (characterized by a yellow/brown discoloration of the solution), the color of the sample solutions were visually examined. As noted in Table 12, adding an approximately equimolar concentration of HCl (50 mM) to the epinephrine bitartate prevented the sample solution from discoloration when stored in glass vials sealed under an ambient environment.

Further, epinephrine in aqueous solutions is also susceptible to conversion of the bioactive stereoisomer (L-epinephrine) to the inactive form (D-epinephrine). Accordingly, the enantiomeric purity of the DMSO solutions was also examined via chiral RP-HPLC. The mobile phase was a 95:5 (v/v) mixture of an aqueous solution (0.20 M NaCl, 0.05% glacial acetic acid) and acetonitrile. A chiral column (Shodex ORpak CDBS-453; 4.6 mm I.D. and 150 mm length) was used with a column temperature of 10° C., a flow rate of 0.5 mL/min, and a 280-nm detection wavelength. Prior to use, the mobile phase was filtered under vacuum through a 0.45-μm nylon filter and the 10 mg/mL sample solutions were diluted 200× with the chiral HPLC mobile phase. The enantiomeric purity (provided as L-epinephrine as a percentage of total epinephrine) is listed in Table 12.

It is important to note that when epinephrine bitartrate was dissolved directly in DMSO, as described in the prior art (e.g. U.S. Pat. No. 9,125,805), the solution exhibited extensive discoloration. The addition of HCl to the formulation inhibited the extent of the discoloration, until at 50 mM added HCl (which is approximately equimolar with the epinephrine molecule), the solution remained clear and colorless throughout the 1 month storage period. At 75 and 100 mM of added HCl, the solutions exhibited significant discoloration.

TABLE 12

Chemical Stability (provided as % epinephrine purity) of 10 mg/mL epinephrine solutions sealed under ambient atmosphere stored at 40° C. and 75% RH for 1 month

| Epinephrine Concentration | Added [HCl] | % Purity | Solution Color | Enantiomeric Purity |
|---|---|---|---|---|
| 10 mg/mL | 0 mM | 92.6% | Red | 100% |
| 10 mg/mL | 1 mM | 94.9% | Dark Pink | 100% |
| 10 mg/mL | 10 mM | 98.5% | Light Pink | 100% |
| 10 mg/mL | 25 mM | 100.0% | Very light Pink | 100% |
| 10 mg/mL | 50 mM | 100.0% | Colorless | 100% |
| 10 mg/mL | 75 mM | 91.6% | Brown | 97.4% |
| 10 mg/mL | 100 mM | 74.8% | Dark Brown | 93.1% |

Example 12

The following example demonstrates the applicability of the present invention to the preparation of stable formulations of small molecules coupled with sealing the sample vials under an inert atmosphere. Epinephrine (from bitartrate) powder (CAS No. 51-42-3) was dissolved to a final API concentration of 10 mg/mL (approximately 55 mM) in DMSO (neat) to which different concentrations of hydrochloric acid (from a 1 N stock solution) had been added. The added concentration of HCl ranged from 1 mM to 100 mM, as shown in Table 13. 0.5 mL aliquots of the epinephrine solutions were stored in 2-mL glass vials and placed in a stability chamber with the temperature of 40° C. and a relative humidity of 75%. These samples were prepared in an ambient environment but were sealed under an inert gas (argon), as Epinephrine is well-known to be susceptible oxidative degradation reactions.

The stability of the small molecule in the formulation and sealed under an inert gas was assessed by RP-HPLC following 1 month of storage and the results are shown in Table 13. Chemical stability was analyzed via HPLC as described in Example 11. As epinephrine solutions are susceptible to degradation-promoted discoloration due, in part, to the conversion of the epinephrine molecule via oxidation to adrenochrome (characterized by a pink discoloration of the solution) and/or melanin (characterized by a yellow/brown discoloration of the solution), the color of the sample solutions were visually examined. As noted in Table 13, sealing the sample vials under an inert gas (argon in this particular example), inhibited the pink discoloration noted above in Example 11, where the sample vials were sealed under an ambient atmosphere. However, upon adding an excess of HCl to the formulation (e.g. significantly above an equimolar concentration relative to the small molecule API) extensive discoloration observed.

As described in Example 11, chiral HPLC analysis was also performed on the argon-backfilled epinephrine samples. Prior to use, the mobile phase was filtered under vacuum through a 0.45-μm nylon filter and the 10 mg/mL sample solutions were diluted 200× with the chiral HPLC mobile phase. The enantiomeric purity (provided as L-epinephrine as a percentage of total epinephrine) is listed in Table 13.

When epinephrine (from bitartrate) was dissolved directly in DMSO and sealed in glass vials under an argon atmosphere, the solution still exhibited discoloration, but the discoloration was mitigated compared to the samples sealed under an ambient environment. The addition of HCl to the formulation inhibited the extent of the discoloration; between 10-50 mM added HCl (the latter of which is approximately equimolar with the epinephrine molecule), the solution remained clear and colorless throughout the 1 month (28 days) storage period. At 75 and 100 mM of added HCl, the solutions were observed to be extensively discolored.

TABLE 13

Chemical Stability (provided as % epinepherin purity) of 10 mg/mL epinephrine solutions sealed under an Argon atmosphere stored at 40° C. and 75% RH for 1 month.

| Epinephrine Concentration | Added [HCl] | % Purity | Solution Color | Enantiomeric Purity |
|---|---|---|---|---|
| 10 mg/mL | 0 mM | 100.0% | Light Pink | 100.0% |
| 10 mg/mL | 1 mM | 100.0% | Very Light Pink | 100.0% |
| 10 mg/mL | 10 mM | 100.0% | Colorless | 100.0% |
| 10 mg/mL | 25 mM | 100.0% | Colorless | 100.0% |
| 10 mg/mL | 50 mM | 100.0% | Colorless | 100.0% |
| 10 mg/mL | 75 mM | 93.9% | Yellow | 97.3% |
| 10 mg/mL | 100 mM | 91.1% | Orange | 91.1% |

All of the compositions and/or methods disclosed and claimed herein can be made and executed without undue experimentation in light of the present disclosure. While the compositions and methods of this disclosure have been described in terms of some embodiments, it will be apparent to those of skill in the art that variations may be applied to the compositions and methods and in the steps or in the sequence of steps of the method described herein without departing from the concept, spirit, and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope, and concept of any invention as defined by the appended claims.

What is claimed is:
1. A stable formulation comprising:
(a) a therapeutic glatiramer or pramlintide peptide, wherein the peptide is not prepared by drying in the presence of a non-volatile buffer;
(b) an ionization stabilizing excipient, wherein the ionization stabilizing excipient is an acid; and
(c) an aprotic polar solvent;
wherein (i) the therapeutic peptide is dissolved in the aprotic solvent in an amount from about 0.1 mg/mL up to the solubility limit of the therapeutic peptide, and (ii) the ionization stabilizing excipient is dissolved in the aprotic polar solvent in an amount to stabilize the ionization of the therapeutic peptide.

2. The formulation of claim 1, wherein the ionization stabilizing excipient is at a concentration of 0.1 mM to less than 100 mM.

3. The formulation of claim 1, wherein the ionization stabilizing excipient is a mineral acid.

4. The formulation of claim 1, wherein the aprotic polar solvent is dimethyl sulfoxide (DMSO).

5. The formulation of claim 1, wherein the aprotic polar solvent is a deoxygenated aprotic polar solvent.

6. The formulation of claim 5, wherein the deoxygenated aprotic polar solvent is deoxygenated DMSO.

7. The formulation of claim 1, wherein the ionization stabilizing excipient is a mineral acid and the aprotic polar solvent is DMSO.

8. The formulation of claim 1, wherein the total moisture content is less than 5% w/w.

9. The formulation of claim 1, further comprising a preservative at less than 10% w/v.

10. The formulation of claim 9, wherein the preservative is benzyl alcohol.

11. The formulation of claim 1, further comprising a sugar alcohol at less than 10% w/v.

12. The formulation of claim 11, wherein the sugar alcohol is mannitol.

* * * * *